(12) United States Patent
Such et al.

(10) Patent No.: US 7,745,553 B2
(45) Date of Patent: Jun. 29, 2010

(54) AQUEOUS DISPERSIONS OF POLYMER PARTICLES

(75) Inventors: Christopher Henry Such, Mount Eliza (AU); Ezio Rizzardo, Wheelers Hill (AU); Algirdas Kazimieras Serelis, Mount Waverley (AU); Brian Stanley Hawkett, Mona Vale (AU); Robert Goulston Gilbert, Newtown (AU); Christopher James Ferguson, Moorabbin (AU); Robert John Hughes, Marden (AU); Edna Olejnik, legal representative, Marden (AU)

(73) Assignee: University of Sydney, New South Wales (AU)

( * ) Notice: Subject to any disclaimer, the term of this patent is extended or adjusted under 35 U.S.C. 154(b) by 1119 days.

(21) Appl. No.: 10/498,502

(22) PCT Filed: Dec. 20, 2002
(Under 37 CFR 1.47)

(86) PCT No.: PCT/AU02/01735

§ 371 (c)(1),
(2), (4) Date: Apr. 6, 2006

(87) PCT Pub. No.: WO03/055919

PCT Pub. Date: Jul. 10, 2003

(65) Prior Publication Data

US 2006/0223936 A1 Oct. 5, 2006

(30) Foreign Application Priority Data

Dec. 21, 2001 (AU) .................................... PR9708
Aug. 14, 2002 (AU) .............................. 2002950772

(51) Int. Cl.
*C08F 2/22* (2006.01)
*C08F 2/38* (2006.01)

(52) U.S. Cl. .................... 526/222; 526/229; 526/219.6; 526/317.1; 526/346; 526/348

(58) Field of Classification Search ................. 526/229, 526/219.6, 222, 317.1, 346, 348
See application file for complete search history.

(56) References Cited

U.S. PATENT DOCUMENTS 7,064,151 B1 * 6/2006 Berge et al. ................. 521/142
2002/0019554 A1 * 2/2002 Benicewicz et al. ......... 558/235

FOREIGN PATENT DOCUMENTS

| EP | 1 205 492 | * | 5/2002 |
| EP | 1 205 492 | A1 | 5/2002 |
| WO | 98/01478 | A1 | 1/1998 |
| WO | WO 98/50436 | * | 11/1998 |
| WO | 99/05099 | A1 | 2/1999 |
| WO | 99/31144 | A1 | 6/1999 |
| WO | WO 00/02939 | A1 | 1/2000 |
| WO | WO 01/77198 | * | 10/2001 |

OTHER PUBLICATIONS

Uzulina et al. "Reversible addition fragmentation transfer (RAFT) polymerization in emulsion", Macromol. Symp. 150, 33-38(2000).*
Hans Gotthardt, et al., "Darstellung und physikalische Eigenschaften mesoionischer 1,3-Dithiolone", Chem. Ber., (1976), No. 109, 1976, pp. 740-752.
Roshan T. A. Mayadunne et al., "Living Polymer by the Use of Trithiocarbonates as Reversible Addition-Fragmentation Chain Transfer (RAFT) Agents: ABA Triblock Copolymers by Radical Polymerization in Two Steps", Macromolecules, American Chemical Society, Washington, DC, US, vol. 33, 2000, pp. 243-245.
PRA Reviews, "Emulsion Polymer Technologies", Jan. 2001, vol. 12, No. 9, 24 pages, John Bently Ed.
Chemical Abstracts, Abstract No. 129:122387 & Tetrahedron: Asymmetry (1998), vol. 9, No. 10, pp. 1641-1644, Chen, Bang-Chi et al., "A new highly enantioselective synthesis of both (R)- and (S)-2-mercaptosuccinic acids".
Chemical Abstracts, Abstract No. 114:229326 & Zhongguo Yiyao Gongye Zazhi (1991), 22(2), 61, Shan Shiming et al., "Synthesis of bucillamine".
Chemical Abstracts, Abstract No. 80:133879 & Makromol. Chem. (1973), 173, 43-65, Kricheldorf, Hans R., et al., "Polymerization of 1,3-dithiolane-2, 4-diones".
Chemical Abstracts, Abstract No. 70:42704 & Tetrahedron (1968), 24(24), 7005-11, Brink, Maud, "N.M.R. spectra of some monosubstituted succinic acids and related compounds".

* cited by examiner

*Primary Examiner*—Ling-Siu Choi
(74) *Attorney, Agent, or Firm*—Arent Fox LLP

(57) ABSTRACT

The invention provides a method for preparing an aqueous dispersion of polymer particles comprising the following steps: (i) preparing a dispersion having a continuous aqueous phase, a dispersed organic phase comprising one or more ethylenically unsaturated monomers, and an amphiphilic RAFT agent as a stabilizer for said organic phase, and (ii) polymerizing said one or more ethylenically unsaturated monomers under the control of said amphiphilic RAFT agent to form said aqueous dispersion of polymer particles, novel amphiphilic RAFT agents for use in this method, novel RAFT agents useful in making these amphiphilic RAFT agents and methods for their manufacture.

12 Claims, No Drawings

AQUEOUS DISPERSIONS OF POLYMER PARTICLES

CROSS-REFERENCE TO RELATED APPLICATION

This application is a National Stage entry of International Application No. PCT/AU02/01735, filed Dec. 20, 2002, the entire specification claims and drawings of which are incorporated herewith by reference.

FIELD OF THE INVENTION

The present invention relates to aqueous dispersions of polymer particles, and in particular to a method of preparing aqueous dispersions of polymer particles using amphiphilic chain transfer agents. The invention also relates to novel amphiphilic chain transfer agents, methods for their preparation and chain transfer agents useful in the preparation of such amphiphilic chain transfer agents.

BACKGROUND OF THE INVENTION

Emulsion polymerisation provides one of the most effective means of preparing an aqueous dispersion of polymer particles. Accordingly, this polymerisation technique has been extensively adopted by industry to manufacture aqueous dispersions suited for use in products such as paints, adhesives, fillers, primers and sealants.

The conventional emulsion polymerisation system initially comprises water, monomer, surfactant and initiator. The emulsion polymerisation process generally commences by dispersing monomer (organic phase) in the water (aqueous phase), with the aid of the surfactant, to provide an emulsion. The initiator, which is usually dissolved in the continuous aqueous phase, provides a source of the free radicals that initiate polymerisation. The dispersed organic phase provides monomer to the propagating polymer chains which in turn form small polymer particles. During formation and in a final form, the polymer particles are stabilized from coalescence by the surfactant. The polymerisation process therefore provides as a product an aqueous dispersion of polymer particles.

Although very useful in providing aqueous dispersions of polymer particles for commercial uses, current emulsion polymerisation technology presents some inherent problems. For example, when a dispersion, or product prepared from a dispersion, is applied to a surface and dries to form a film, as with a paint, free surfactant in the dispersion can tend to migrate to the surface and localise in pockets, thereby adversely affecting the surface properties of the film, particularly in the area of water sensitivity. Also, polymerisation is typically achieved by a classical free radical polymerisation process which has a limited capacity to effectively control both molecular weight and architecture of the resulting polymer, and no ability to produce block copolymers.

One approach to restricting migration of the surfactants has been to use amphiphilic compounds that have an unsaturated hydrophobic tail, so called "surfmers". During polymerisation, the surfmers stabilize monomer, allowing the polymer particles to grow in a conventional manner. The unsaturated hydrophobic tail, which becomes buried within a growing polymer particle, can react with a propagating chain to effectively anchor the surfmer to the particle. However, the use of such a technique provides little ability to control the architecture of the resultant polymer particles.

Options for modifying the radical chemistry of the polymerisation reaction have been quite limited. However, recent developments in free radical chemistry have to some extent broadened the scope of chemistry available for potential adaptation to emulsion polymerisation. In particular, so called controlled/living radical polymerisation techniques such as nitroxide mediated radical polymerisation (NMRP), atom transfer living polymerisation (ATRP), degenerative transfer techniques best exemplified by reversible addition-fragmentation chain transfer (RAFT) have been investigated (Macromolecules 2001, 34, 5885-5896).

The RAFT process, as described in International Patent publication WO 98/01478, is a radical polymerisation technique that enables polymers to be prepared having a well defined molecular architecture and a low polydispersity. The technique employs a chain transfer agent (CTA or RAFT agent) of the general formula (1):

which has been proposed to react with a propagating radical $(P_n^*)$ in accordance with Scheme 1.

Scheme 1.
Proposed mechanism of RAFT polymerisation

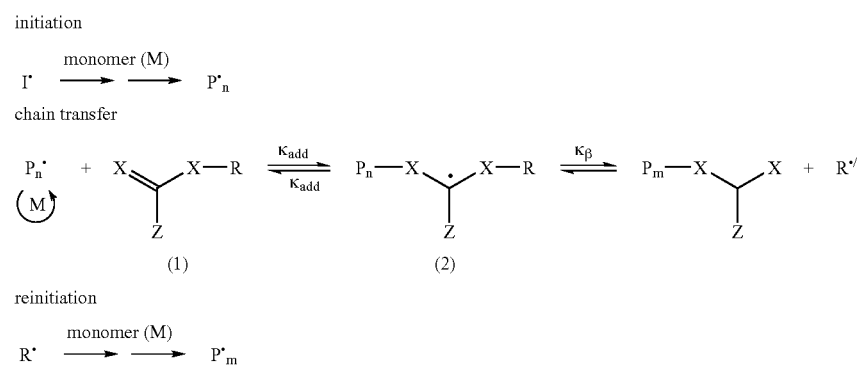

chain equilibrium

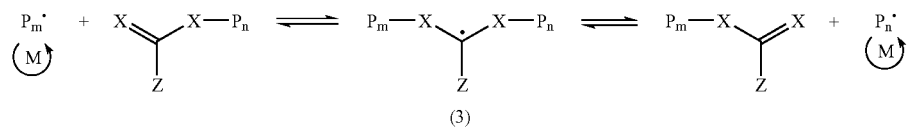

(3)

termination $P_n^{\bullet} + P_m^{\bullet} \longrightarrow$ dead polymer

The effectiveness of the chain transfer agent (1) is believed to depend on a complex array of rate constants. In particular, the formation of polymer according to scheme 1 is believed to be reliant upon equilibria that require high rate constants for the addition of propagating radicals to agent (1) and the fragmentation of intermediate radicals (2) and (3), relative to the rate constant for propagation.

The rate constants associated with RAFT polymerisation are influenced by a complex interplay between stability, steric and polarity effects in the substrate, the radicals and the products formed. The polymerisation of specific monomers and combinations of monomers will introduce different factors and structural preferences for the reagent 1. The interplay of factors for a particular system have been largely rationalised on the basis of the results obtained. A clear definition of all factors that influence polymerisation for any particular system has not yet been determined.

While RAFT technology provides for the preparation of block copolymers using free radical polymerisation, and can provide means for superior control over many polymerisation processes, difficulties have been encountered in using the technology in emulsion, miniemulsion, suspension polymerisation processes and the like. Successful adaptation of RAFT chemistry to an emulsion polymerisation requires the polymerisation conditions to be such that the polymerisation process can proceed under RAFT control. Furthermore, in order to maintain control over polydispersity and molecular weight, the RAFT agent must be located at the reaction loci (nucleated particles) at the start of the polymerisation and be homogeneously distributed amongst all particles. To achieve these conditions, a RAFT agent should be sufficiently water-soluble so as to diffuse from a monomer droplet to a nucleated polymer particle in a time frame that is much faster than the duration of the polymerisation and which is also much faster than the nucleation period. Alternatively, a water miscible co-solvent could be used to aid the migration of the RAFT agent. Such requirements may be met by "fine tuning" the reaction system, but this is difficult to achieve in practice.

Alternative modes of performing an emulsion polymerisation, such as miniemulsion or seed emulsion techniques, have recently been shown to alleviate problems associated with the diffusion of RAFT agents. In both cases, the RAFT agent can be directly and uniformly introduced to the polymerisation loci prior to starting the reaction, thereby satisfying the aforementioned requirements. Such techniques have been shown to provide superior control over the polymerisation process compared with classical free radical polymerisation. However, both techniques employ conventional surfactants and dispersions prepared thereby are subject to the aforementioned surfactant migration problems. Furthermore, both techniques require co-surfactant stabilizers and other additives which introduce unwanted components into the polymerising mixture and compromise the properties of the finished product to a point where the potential benefits of the RAFT process cannot be demonstrated.

SUMMARY OF THE INVENTION

It would therefore be desirable to provide a method for producing an aqueous dispersion of polymer particles which can exhibit the advantages of RAFT polymerisation using conventional emulsion polymerisation techniques without the need for conventional surfactants.

Accordingly, in a first aspect the present invention provides a method for preparing an aqueous dispersion of polymer particles comprising the following steps:

(i) preparing a dispersion having a continuous aqueous phase, a dispersed organic phase comprising one or more ethylenically unsaturated monomers, and an amphiphilic RAFT agent as a stabilizer for said organic phase, and (ii) polymerising said one or more ethylenically unsaturated monomers under the control of said amphiphilic RAFT agent to form said aqueous dispersion of polymer particles.

In a second aspect the present invention provides an amphiphilic RAFT agent of general formula (4a)

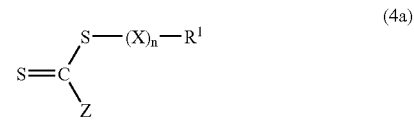

(4a)

where each X is independently a residue of a polymerisable monomer;

n is 1 to 100;

$R^1$ is $-CH(CH_3)COOH$, $-CH(CO_2H)CH_2CO_2H$, or $-CH(CH_3)CONR^aR^b$, where $R^a$ and $R^b$ are the same or different and independently selected from H, $C_1$-$C_6$ alkyl, $C_1$-$C_6$ alkoxy, $C_6$-$C_{12}$ aryl, $C_7$-$C_{18}$ alkylaryl or $C_6$-$C_{12}$ heteroaryl, each of which is substituted with one or more hydrophilic groups selected from $-CO_2H$, $-CO_2R'$, $-SO_3H$, $-OSO_3H$, $-SOR'$, $-SO_2R'$, $-OP(OH)_2$, $-P(OH)_2$, $-PO(OH)_2$, $-OH$, $-OR'$, $-(OCH_2-CHR)_w-OH$, $-CONH_2$, CONHR', CONR'R'', $-NR'R''$, $-N^+R'R''R'''$, where R is selected from $C_1$-$C_6$ alkyl, w is 1 to 10, R', R'' and R''' are independently selected from $C_1$-$C_6$ alkyl and $C_6$-$C_{12}$ aryl which are optionally substituted with one or more hydrophilic substituents selected from $-CO_2H$, $-SO_3H$, $-OSO_3H$, $-OH$, $-(COCH_2CHR)_w-OH$, $-CONH_2$, $-SOR$ and $SO_2R$, and salts thereof; and Z is selected from optionally substituted alkyl, optionally substituted aryl, optionally substituted arylalkyl, optionally substituted alkylthio, optionally substituted arylthio, optionally substituted arylalkylthio, and optionally substituted acylamino.

In a third aspect the present invention provides a RAFT agent of general formula (5a)

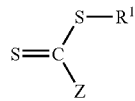

(5a)

where R¹ is —CH(CH₃)COOH, —CH(CO₂H)CH₂CO₂H, or —CH(CH₃)CONR$^a$R$^b$, where R$^a$ and R$^b$ are the same or different and independently selected from H, $C_1$-$C_6$ alkyl, $C_1$-$C_6$ alkoxy, $C_6$-$C_{12}$ aryl, $C_7$-$C_{18}$ alkylaryl or $C_6$-$C_{12}$ heteroaryl, each of which is substituted with one or more hydrophilic groups selected from —CO₂H, —CO₂R', —SO₃H, —OSO₃H, —SOR', —SO₂R', —OP(OH)₂, —P(OH)₂, —PO(OH)₂, —OH, —OR', —(OCH₂—CHR)$_w$—OH, —CONH₂, CONHR', CONR'R", —NR'R", —N⁺R'R"R"', where R is selected from $C_1$-$C_6$ alkyl, w is 1 to 10, R', R" and R"' are independently selected from $C_1$-$C_6$ alkyl and $C_6$-$C_{12}$ aryl which are optionally substituted with one or more hydrophilic substituents selected from —CO₂H, —SO₃H, —OSO₃H, —OH, —(COCH₂CHR)$_w$—OH, —CONH₂, —SOR and SO₂R, and salts thereof; and Z is selected from optionally substituted alkyl, optionally substituted aryl, optionally substituted arylalkyl, optionally substituted alkylthio, optionally substituted arylthio, optionally substituted arylalkylthio, and optionally substituted acylamino.

It is to be understood that while the second and third aspects of the invention are not intended to encompass known RAFT agents, the first aspect of the invention relates to the use of any suitable amphiphilic RAFT agent, even those which may have been described in the prior art.

In a fourth aspect the invention provides a method of preparing RAFT agents by conjugate addition of a dithiocarbonyl compound to an α,β-unsaturated carbonyl or thiocarbonyl compound.

DESCRIPTION OF THE PREFERRED EMBODIMENTS

As used herein, unless otherwise stated, the term "aqueous dispersion" denotes a polyphasic system having a dispersed organic phase and a continuous aqueous phase. The organic phase may be a monomer phase, a polymer phase or a mixture thereof and may include other liquid, solid or semi-solid components known to the art, such as pigments, stabilizers and plasticizers. The organic phase may also be a polyphasic system, such as a water-in-oil emulsion. Where the organic phase is a liquid the dispersion may also be referred to as an emulsion. When the organic phase is a solid or semi-solid then the dispersion may be referred to as a colloidal suspension. In the surface coating field such colloidal suspensions are often referred to as emulsions, and the process for preparing them is called emulsion polymerisation, although a more accurate term for the final aqueous dispersion of polymer particles is "latex".

As used herein, unless otherwise stated, the term "amphiphilic RAFT agent" refers to a RAFT agent that has a structure with both hydrophilic and hydrophobic regions such that the agent exhibits surfactant like properties.

As used herein, unless otherwise stated, the term "stabilizer" denotes an amphiphilic compound capable of stabilizing a dispersion from coalescing. Where the stabilizer is acting to stabilize a dispersed liquid organic phase in a continuous aqueous phase the stabilizer may also be referred to as an emulsifier.

Accordingly, a reference to an amphiphilic RAFT agent acting as a stabilizer is a reference to an amphiphilic RAFT agent that stabilizes a dispersion from coalescing, or forms a micelle. The method by which the amphiphilic RAFT agent achieves stabilization of the dispersed organic phase in the aqueous medium will depend largely on the polymerization method utilized. For example, in a conventional emulsion polymerization process according to the invention it is believed that polymerization of amphiphilic RAFT agent with added monomer in the aqueous medium produces a dispersion of stabilized organic phase in the aqueous medium. The stabilized organic phase comprises monomer and amphiphilic RAFT agent which, due to the polymerization, is rendered non-labile (i.e. not freely exchanging with other dispersed organic phases or dissolving in the surrounding aqueous phase). In suspension polymerization or mini emulsion techniques the stabilization by the amphiphilic RAFT agent is believed to occur, at least initially, in much the same way as conventional surfactants or stabilizing agents.

The method of the present invention advantageously provides the ability to form an aqueous dispersion of polymer particles without the need for conventional surfactants. In addition, the method provides means for forming the polymer particles under RAFT controlled polymerisation.

The present invention contemplates a method for preparing a wide array of aqueous dispersions of polymer particles. In particular, the method is particularly suited to preparing dispersions for use in paint, sealant, primer and adhesive applications.

The method of the present invention can be used in conventional emulsion, miniemulsion and suspension polymerisation processes. In all such processes it is preferred that the amphiphilic RAFT agent does not associate with or stabilize reservoir monomer droplets in the aqueous phase that ultimately are not destined to develop into a polymer particle. Should this occur, it is believe that control over the molecular weight and polydispersity of the resulting polymer particles will be adversely effected. To minimise or avoid this association or stabilization of reservoir monomer droplets, the way in which the dispersion in step (i) of the method of the present invention is prepared may vary depending upon the polymerisation method employed. For example, in conventional emulsion polymerisation it is preferred that the dispersion of step (i) is prepared by forming a solution of amphiphilic RAFT agent in water and polymerising added ethylenically unsaturated monomer under the control of the amphiphilic RAFT agent.

When applied to emulsion polymerisation, it is also preferred that the addition of monomer is limited so as to avoid the formation of monomer droplets in the water until the water soluble RAFT agents have undergone sufficient polymerisation with monomer to become water insoluble. It is believed that this approach renders the amphiphilic RAFT agent non-labile, producing a stabilized organic phase which for convenience will hereinafter be referred to as a non-labile micelle. This is believed to effectively prevent the amphiphilic RAFT agents from migrating individually through the aqueous phase, and therefore reduces potential for the agents to associate with or stabilize reservoir monomer droplets in the water phase. Accordingly, at this stage further monomer can be added at a greater rate to swell the non-labile micelles without forming "stabilized" monomer droplets in the aqueous phase. The resulting swollen micelle, or dispersed organic phase comprising monomer, is conveniently stabilized from coalescing by the amphiphilic RAFT agents, and can facilitate further polymerisation of monomer to form the desired aqueous dispersion of polymer particles.

If additional amphiphilic RAFT agent is added during the conventional emulsion polymerisation of new or growing particles, it is also preferred that the amphiphilic RAFT agent is water soluble and that the rate of addition of monomer during the addition of amphiphilic RAFT agent is limited so as to avoid formation of reservoir monomer droplets in the aqueous phase.

The method of the present invention, when applied to conventional emulsion polymerisation, preferably carried out as a continuous or semi-continuous addition process rather than as a batch process. In this regard, a batch process is likely to result in the situation where amphiphilic RAFT agent can associate with or stabilize monomer droplets that ultimately will not develop into a polymer particle. If a batch process is to be used, it is preferable that a miniemulsion technique is used.

In the case of miniemulsion and suspension polymerisation, it is preferred that the dispersion of step (i) of the method of the present invention is prepared by forming a composition comprising water insoluble amphiphilic RAFT agent and ethylenically unsaturated monomer and combining this composition with water. Preferably, the amphiphilic RAFT agents in this case are dissolved in the monomer. An alternative preferred way in which the dispersion of step (i) may be prepared involves forming a composition comprising water insoluble amphiphilic RAFT agent and water, and combining this composition with ethylenically unsaturated monomer. By using water insoluble amphiphilic RAFT agents, it is believed that the agents essentially become irreversibly associated with the monomer and are effectively prevented from migrating individually through the water phase. As discussed above, this effect reduces the potential for the agents to associate with or stabilize reservoir monomer droplets in the water phase.

By "composition" is meant a collective of components that when combined form a solution, dispersion or mixture.

When reference is made to "combining this composition", it is meant that the composition is combined so as to form the dispersion. In this regard, means for promoting the formation of a dispersion, such as applying shear to the combined composition, are well known in the art. In the case of forming a composition comprising water insoluble amphiphilic RAFT agent and water, it may be necessary to subject this composition to means for forming a dispersion before the composition is combined with ethylenically unsaturated monomer.

Generally, a water insoluble amphiphilic RAFT agent would not form a clear solution when added to water.

In the case of miniemulsion and suspension polymerisation, it is also preferable that sufficient amphiphilic RAFT is used to stabilize substantially all of the monomer present. By this approach, all monomer droplets should become particles and reservoir monomer droplets are substantially avoided. Accordingly, in contrast to a conventional emulsion process, it is preferable that these processes are carried out as a batch process. However, where the polymerisation is carried out as a batch process, it is preferable that substantially no water soluble amphiphilic RAFT agent is present at any time during the reaction. However a miniemulsion carried out initially as a batch process can be subsequently adapted to proceed as a continuous addition process through addition of further monomer and amphiphilic RAFT agent. Under these circumstances, it is preferable to add water soluble RAFT agents, and that the addition occurs at such a time where substantially all of the monomer present is either dissolved in the water phase or solvated in polymer that has been formed. Once this state has been achieved, further monomer and water soluble RAFT agent can be added to the reaction system. However, in this case it is preferred that monomer is added at such rate to avoid formation of free monomer droplets while there are still water soluble RAFT agents present.

Where the method of the present invention is applied in miniemulsion and suspension polymerisation, it is also possible to incorporate preformed polymer and/or solid particles within the dispersed phase of polymer particles. Furthermore, although less preferred, it is also possible to conduct miniemulsion polymerisations in the presence of water soluble amphiphilic RAFT agents.

Amphiphilic RAFT agents suitable for use in the present invention include those of general formula (4):

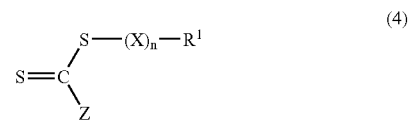

(4)

where each X is independently a polymerised residue of an ethylenically unsaturated monomer, n is an integer ranging from 0 to 100, preferably from 0 to 60, most preferably from 0 to 30, $R^1$ is an organic group optionally substituted with one or more hydrophilic groups and Z is any group that can promote sufficient reactivity of the thiocarbonyl group towards radical addition while not slowing the rate of fragmentation to the extent that there is unacceptable retardation of polymerisation. Preferred $R^1$ groups $C_1$-$C_6$ alkyl, $C_1$-$C_6$ alkoxy aryl or heteroaryl, each of which is substituted with one or more hydrophilic groups selected from —$CO_2H$, —$CO_2R'$, —$SO_3H$, —$OSO_3H$, —SOR', —$SO_2R'$, —OP(OH)$_2$, —P(OH)$_2$, —PO(OH)$_2$, —OH, —OR', —(OCH$_2$—CHR)$_w$—OH, —CONH$_2$, CONHR', CONR'R", —NR'R", —N$^+$R'R"R'", where R is selected from $C_1$-$C_6$ alkyl, w is 1 to 10, R', R" and R'" are independently selected from alkyl and aryl which are optionally substituted with one or more hydrophilic substituents selected from —$CO_2H$, —$SO_3H$, —$OSO_3H$, —OH, —(COCH$_2$CHR)$_w$—OH, —CONH$_2$, —SOR and SO$_2$R, and salts thereof. Particularly preferred $R^1$ groups include, but are not limited to, —CH(CH$_3$)CO$_2$H, —CH(CO$_2$H)CH$_2$CO$_2$H, —C(CH$_3$)$_2$CO$_2$H. Preferred Z groups include, optionally substituted alkoxy, optionally substituted aryloxy, optionally substituted alkyl, optionally substituted aryl, optionally substituted heterocyclyl, optionally substituted arylalkyl, optionally substituted alkylthio, optionally substituted arylalkylthio, dialkoxy- or diaryloxy-phosphinyl [—P(=O)OR$^2_2$], dialkyl- or diaryl-phosphinyl [—P(=O)R$^2_2$], optionally substituted acylamino, optionally substituted acylimino, optionally substituted amino, $R^1$—(X)$_n$—S— and a polymer chain formed by any mechanism; wherein $R^1$; X and n are as defined above and $R^2$ is selected from the group consisting of optionally substituted $C_1$-$C_{18}$ alkyl, optionally substituted $C_2$-$C_{18}$ alkenyl, optionally substituted aryl, optionally substituted heterocyclyl, optionally substituted aralkyl, optionally substituted alkaryl. Particularly preferred Z groups include, but are not limited to, —CH$_2$(C$_6$H$_5$), C$_1$-C$_{20}$ alkyl,

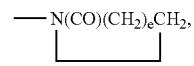

where e is 2 to 4, and —SR$^3$, where R$^3$ is selected from $C_1$ to $C_{20}$ alkyl.

Preferred optional substituents for $R^2$ and Z groups include epoxy, hydroxy, alkoxy, acyl, acyloxy, carboxy (and salts), sulfonic acid (and salts), alkoxy- or aryloxy-carbonyl, isocyanato, cyano, silyl, halo, and dialkylamino.

In selecting both $R^1$ and Z groups for amphiphilic RAFT agents of formula (4), those agents resulting from any combination of particularly preferred $R^1$ and Z groups are also particularly preferred. Where the hydrophilic group is —N$^+$R'R''R''' there will be an associated counter anion.

Other suitable amphiphilic RAFT agents include those of formula (4) above in which $R^1$ is an organic group, optionally substituted with one or more hydrophobic groups. In this case, Z is preferably an organic group optionally substituted with one or more hydrophilic groups.

The terms "aryl" and "heteroaryl" as used herein refer to any substituent which includes or consists of one or more aromatic or heteroaromatic ring respectively, and which is attached via a ring atom. The rings may be mono or polycyclic ring systems, although mono or bicyclic 5 or 6 membered rings are preferred. Examples of suitable rings include but are not limited to benzene, biphenyl, terphenyl, quaterphenyl, naphthalene, tetrahydronaphthalene, 1-benzylnaphthalene, anthracene, dihydroanthracene, benzanthracene, dibenzanthracene, phenanthracene, perylene, pyridine, 4-phenylpyridine, 3-phenylpyridine, thiophene, benzothiophene, naphthothiophene, thianthrene, furan, benzofuran, pyrene, isobenzofuran, chromene, xanthene, phenoxathiin, pyrrole, imidazole, pyrazole, pyrazine, pyrimidine, pyridazine, indole, indolizine, isoindole, purine, quinoline, isoquinoline, phthalazine, quinoxaline, quinazoline, pteridine, carbazole, carboline, phenanthridine, acridine, phenanthroline, phenazine, isothiazole, isooxazole, phenoxazine and the like, each of which may be optionally substituted In this specification "optionally substituted" means that a group may or may not be further substituted with one or more groups selected from, but not limited to, alkyl, alkenyl, alkynyl, aryl, halo, haloalkyl, haloalkenyl, haloalkynyl, haloaryl, hydroxy, alkoxy, alkenyloxy, aryloxy, benzyloxy, haloalkoxy, haloalkenyloxy, acetyleno, carboximidyl, haloaryloxy, isocyano, cyano, formyl, carboxyl, nitro, nitroalkyl, nitroalkenyl, nitroalkynyl, nitroaryl, alkylamino, dialkylamino, alkenylamino, alkynylamino, arylamino, diarylamino, benzylamino, imino, alkylimine, alkenylimine, alkynylimino, arylimino, benzylimino, dibenzylamino, acyl, alkenylacyl, alkynylacyl, arylacyl, acylamino, diacylamino, acyloxy, alkylsulphonyloxy, arylsulphenyloxy, heterocyclyl, heterocycloxy, heterocyclamino, haloheterocyclyl, alkylsulphonyl, arylsulphonyl, alkylsolphinyl, arylsulphinyl, carboalkoxy, alkylthio, benzylthio, acylthio, sulphonamido, sulfanyl, sulfo and phosphorus-containing groups, alkoxysilyl, silyl, alkylsilyl, alkylalkoxysilyl, phenoxysilyl, alkylphenoxysilyl, alkoxyphenoxysilyl, arylphenoxysilyl, allophanyl, guanidino, hydantoyl, ureido, and ureylene.

The terms "halogen" and "halo" as used herein, unless otherwise specified, refer to I, Br, Cl and F.

In the above definitions, the term "alkyl", used either alone or in compound words such as "alkenyloxyalkyl", "alkylthio", "alkylamino" and "dialkylamino" denotes straight chain, branched or cyclic alkyl, preferably $C_{1-20}$ alkyl or cycloalkyl. Examples of straight chain and branched alkyl include methyl, ethyl, propyl, isopropyl, butyl, isobutyl, secbutyl, tertbutyl, amyl, isoamyl, sec-amyl, 1,2-dimethylpropyl, 1,1-dimethyl-propyl, hexyl, 4-methylpentyl, 1-methylpentyl, 2-methylpentyl, 3-methylpentyl, 1,1-dimethylbutyl, 2,2-dimethylbutyl, 3,3-dimethylbutyl, 1,2-dimethylbutyl, 1,3-dimethylbutyl, 1,2,2,-trimethylpropyl, 1,1,2-trimethylpropyl, heptyl, 5-methoxyhexyl, 1-methylhexyl, 2,2-dimethylpentyl, 3,3-dimethylpentyl, 4,4-dimethylpentyl, 1,2-dimethylpentyl, 1,3-dimethylpentyl, 1,4-dimethyl-pentyl, 1,2,3,-trimethylbutyl, 1,1,2-trimethylbutyl, 1,1,3-trimethylbutyl, octyl, 6-methylheptyl, 1-methylheptyl, 1,1,3,3-tetramethylbutyl, nonyl 1-, 2-, 3-, 4-, 5-, 6- or 7-methyl-octyl, 1-, 2-, 3-, 4- or 5-ethylheptyl, 1-, 2- or 3-propylhexyl, decyl, 1-, 2-, 3-, 4-, 5-, 6-, 7 - and 8-methylnonyl, 1-, 2-, 3-, 4-, 5- or 6-ethyloctyl, 1-, 2-,3- or 4-propylheptyl, undecyl, 1-, 2-, 3-, 4-, 5-, 6-, 7-, 8- or 9-methyldecyl, 1-, 2-, 3-, 4-, 5-, 6- or 7-ethylnonyl, 1-, 2-, 3-, 4- or 5-propyloctyl, 1-, 2- or 3-butylheptyl, 1-pentylhexyl, dodecyl, 1-, 2-, 3-, 4-, 5-, 6-, 7-, 8-, 9- or 10-methylundecyl, 1-, 2-, 3-, 4-, 5-, 6-, 7- or 8-ethyldecyl, 1-, 2-, 3-, 4-, 5- or 6-propylnonyl, 1-, 2-, 3- or 4-butyloctyl, 1-2-pentylheptyl and the like. Examples of cyclic alkyl include mono- or polycyclic alkyl groups such as cyclopropyl, cyclobutyl, cyclopentyl, cyclohexyl, cycloheptyl, cyclooctyl, cyclononyl, cyclodecyl and the like.

The term "salt" denotes a species in ionised form, and includes both acid addition and base addition salts. In the context of the present invention, suitable salts are those that do not interfere with the RAFT chemistry.

The term "counter anion" denotes a species capable of providing a negative charge to balance the charge of the corresponding cation. Examples of counter anions include, $Cl^-$, $I^-$, $Br^-$, $F^-$, $NO_3^-$, $CN^-$ and $PO_3^-$, The term "alkoxy" denotes straight chain or branched alkoxy, preferably $C_{1-20}$ alkoxy. Examples of alkoxy include methoxy, ethoxy, n-propoxy, isopropoxy and the different butoxy isomers.

The term "alkenyl" denotes groups formed from straight chain, branched or cyclic alkenes including ethylenically mono-, di- or poly-unsaturated alkyl or cycloalkyl groups as previously defined, preferably $C_{2-20}$ alkenyl. Examples of alkenyl include vinyl, allyl, 1-methylvinyl, butenyl, iso-butenyl, 3-methyl-2-butenyl, 1-pentenyl, cyclopentenyl, 1-methyl-cyclopentenyl, 1-hexenyl, 3-hexenyl, cyclohexenyl, 1-heptenyl, 3-heptenyl, 1-octenyl, cyclooctenyl, 1-nonenyl, 2-nonenyl, 3-nonenyl, 1-decenyl, 3-decenyl, 1,3-butadienyl, 1-4,pentadienyl, 1,3-cyclopentadienyl, 1,3-hexadienyl, 1,4-hexadienyl, 1,3-cyclohexadienyl, 1,4-cyclohexadienyl, 1,3-cycloheptadienyl, 1,3,5-cycloheptatrienyl and 1,3,5,7-cyclooctatetraenyl.

The term "alkynyl" denotes groups formed from straight chain, branched or cyclic alkyne including those structurally similar to the alkyl and cycloalkyl groups as previously defined, preferably $C_{2-20}$ alkynyl. Examples of alkynyl include ethynyl, 2-propynyl and 2- or 3-butynyl.

The term "acyl" either alone or in compound words such as "acyloxy", "acylthio", "acylamino" or "diacylamino" denotes carbamoyl, aliphatic acyl group and acyl group containing an aromatic ring, which is referred to as aromatic acyl or a heterocyclic ling which is referred to as heterocyclic acyl, preferably $C_{1-20}$ acyl. Examples of acyl include carbamoyl; straight chain or branched alkanoyl such as formyl, acetyl, propanoyl, butanoyl, 2-methylpropanoyl, pentanoyl, 2,2-dimethylpropanoyl, hexanoyl, heptanoyl, octanoyl, nonanoyl, decanoyl, undecanoyl, dodecanoyl, tridecanoyl, tetradecanoyl, pentadecanoyl, hexadecanoyl, heptadecanoyl, octadecanoyl, nonadecanoyl and icosanoyl; alkoxycarbonyl such as methoxycarbonyl, ethoxycarbonyl, t-butoxycarbonyl, t-pentyloxycarbonyl and heptyloxycarbonyl; cycloalkylcarbonyl such as cyclopropylcarbonyl, cyclobutylcarbonyl, cyclopentylcarbonyl and cyclohexylcarbonyl; alkylsulfonyl such as methylsulfonyl and ethylsulfonyl; alkoxysulfonyl such as methoxysulfonyl and ethoxysulfonyl; aroyl such as benzoyl, toluoyl and naphthoyl; aralkanoyl such as phenylalkanoyl (e.g. phenylacetyl, phenylpropanoyl, phenylbutanoyl, phenylisobutylyl, phenylpentanoyl and phenylhexanoyl) and naphthylalkanoyl (e.g. naphthylacetyl, naphthylpropanoyl and naphthylbutanoyl; aralkenoyl such as phenylalkenoyl (e.g. phenylpropenoyl, phenylbutenoyl, phenylmethacryloyl, phenylpentenoyl and phenylhexenoyl and naphthylalkenoyl (e.g. naphthylpropenoyl, naphthylbutenoyl and naphthylpentenoyl); aralkoxycarbonyl such as phenylalkoxycarbonyl (e.g. benzyloxycarbonyl); aryloxycarbonyl such as phenoxycarbonyl and napthyloxycarbonyl; aryloxyalkanoyl such as phenoxyacetyl and phenoxypropionyl; arylcarbamoyl such as phenylcarbamoyl; arylthiocarbamoyl such as phenylthiocarbamoyl; arylglyoxyloyl such as phenylglyoxyloyl and naphthylglyoxyloyl; arylsulfonyl such as phenylsulfonyl and napthylsulfonyl; heterocycliccarbonyl; heterocyclicalkanoyl such as thienylacetyl, thienylpropanoyl, thienylbutanoyl, thienylpentanoyl, thienylhexanoyl, thiazolylacetyl, thiadiazolylacetyl and tetrazolylacetyl; heterocyclicalkenoyl such as heterocyclicpropenoyl, heterocyclicbutenoyl, heterocyclicpentenoyl and heterocyclichexenoyl; and heterocyclicglyoxyloyl such as thiazolylglyoxyloyl and thienylglyoxyloyl.

The terms "heterocyclic", "heterocyclyl" and "heterocycl" as used herein on their own or as part of a term such as "heterocyclicalkenoyl", heterocycloxy" or "haloheterocyclyl" refer to aromatic, pseudo-aromatic and non-aromatic rings or ring systems which contain one or more heteroatoms selected from N, S, and O and which may be optionally substituted. Preferably the rings or ring systems have 3 to 20 carbon atoms. The rings or ring systems may be selected from those described above in relation to the definition of "heteroaryl".

Most preferred amphiphilic RAFT agents include, but are not limited to, the following compounds:

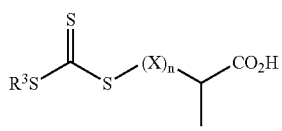 (6)

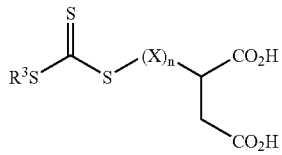 (7)

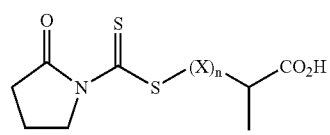 (8)

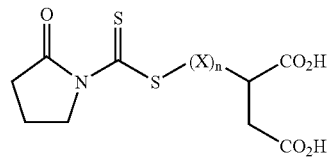 (9)

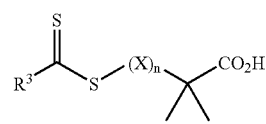 (10)

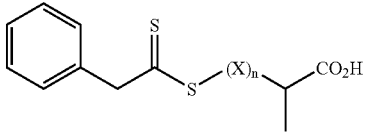 (11)

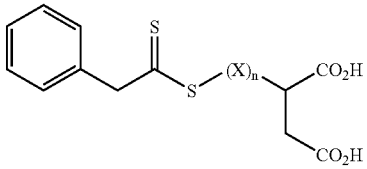 (12)

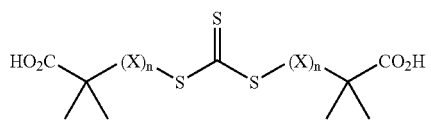 (22)

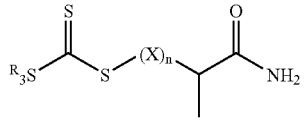 (23)

where $R^3$; X and n are as previously defined.

When selecting an amphiphilic RAFT for use in accordance with the method of the present invention, it is preferable that it demonstrates hydrolytic stability under the conditions of the polymerisation. In this regard, trithiocarbonyl amphiphilic RAFT agents are particularly preferred.

An important feature of amphiphilic RAFT agents with formula (4) is the nature of their amphiphilic character. Amphiphilic character may be provided through different combinations of hydrophilic and hydrophobic regions. Preferably, the amphiphilic RAFT agents derive their amphiphilic character from either:

1) a combination of a hydrophobic end and a hydrophilic end; wherein the Z group provides hydrophobic properties to one end, and $R^1$ and —$(X)_n$— provide hydrophilic properties to the other end. In this case —$(X)_n$— may be derived from hydrophilic monomer or be a tapered copolymer which gets progressively hydrophilic towards $R^1$; or 2) a combination of a hydrophobic end and a hydrophilic end; wherein the Z group provides hydrophilic properties to one end, and $R^1$ and —$(X)_n$— provide hydrophobic properties to the other end. In this case —$(X)_n$— may be derived from hydrophobic monomer or may be a tapered copolymer which gets progressively hydrophobic towards $R^1$; or 3) a combination of a hydrophobic end and a hydrophilic end; wherein the Z group and —$(X)_n$— provide hydrophobic properties to one end, and $R^1$ provides hydrophilic properties to the other end; or 4) a combination of a hydrophobic end and a hydrophilic end; wherein the Z group provides hydrophobic properties to one end, —$(X)_n$— provides hydrophilic properties to the other end, and $R^1$ is hydrophobic such that the net effect of —$(X)_n$— and $R^1$ is to provide hydrophilic character to that end; or 5) a combination of hydrophilic ends and a hydrophobic middle section, wherein Z=—S—$(X)_n$—$R^1$, wherein each $R^1$ may be the same or different and provides hydrophilic properties to each end, and wherein —(X)—$_n$ provides hydrophobic properties to the middle section; or 6) a combination of hydrophobic and hydrophilic properties within —(X)$_n$; wherein the portion of the —(X)$_n$— group closest to $R^1$ provides the hydrophilic properties and the portion of the —(X)$_n$— group closest to the thiocarbonylthio group provides the hydrophobic properties. In this case, —(X)$_n$— of formula (4) may be further represented as -(A)$_m$-(B)$_o$- to provide a block copolymer that has the following general formula (13):

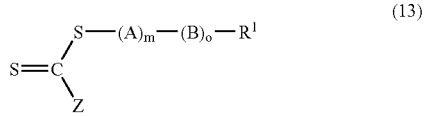

(13)

where formula (13) is a subset of formula (4) where (X)$_n$ is -(A)$_m$-(B)$_o$— and where each A and B is independently a polymerised residue of an ethylenically unsaturated monomer such that -(A)$_m$— provides hydrophobic properties and —(B)$_o$— provides hydrophilic properties, and m and o are integers ranging from 1 to 99, preferably from 1 to 50, more preferably from 1 to 30, most preferably from 1 to 15, and Z is as described above. Z may also be chosen such that its polarity combines with that of -(A)$_m$- to enhance the overall hydrophobic character to that end of the RAFT agent. In addition to the hydrophilic character provided by —(B)$_o$—, $R^1$ may also be hydrophilic and enhance the overall hydrophilic character to that end of the RAFT agent, or $R^1$ may be hydrophobic provided that the net effect of —(B)$_o$- and $R^1$ results in an overall hydrophilic character to that end of the RAFT agent; or 7) a combination of hydrophilic ends and a hydrophobic middle section, wherein Z, of general formula (13), is —S-(A)$_m$-(B)$_o$—$R^1$, where -(A)$_m$ and —(B)$_o$— are as defined above. Each $R^1$ may be the same or different and the combination of —(B)$_o$—$R^1$ provides an overall hydrophilic properties to one end, and the combination of —(B)$_o$—$R^2$ provides an overall hydrophilic properties to the other end. The hydrophobic portion of this type of amphiphic RAFT agent is derived from -(A)$_m$—.

Preferably, amphiphilic RAFT agents used in accordance with the method of the present invention are chosen such that their amphiphilic character is tailored to suit the particular mode of emulsion polymerisation to be employed. In this regard, integers m and o defined in general formula (13) may be selected such that:

i) for conventional emulsion polymerisation, m preferably ranges from 1 to 20, more preferably 1 to 15 and most preferably 1 to 10 (being at lower values within those preferred ranges for more hydrophobic monomers, and at higher values within these preferred ranges for less hydrophobic monomers); o preferably ranges from 1 to 30, more preferably 1 to 10 and most preferably 1 to 5 if (B) is derived from an ionic monomer; and o preferably ranges from 1 to 80, more preferably 1 to 40 and most preferably 1 to 30 if (B) is derived from a non ionic monomer;

ii) for miniemulsion and suspension polymerisation, m is 1 or greater, preferably m is 5 or greater, more preferably m is 10 or greater; o is as defined above for conventional emulsion polymerisation.

It is recognised that the limits defined for the amphiphilic RAFT agents or this invention are those necessary for them to become adequate stabilizers for the aqueous dispersion of the organic phase. Generally further polymerisation of monomers or various types would yield values of n limited by the amount of polymer polymerised per active RAFT agent. Such values of n can be substantially greater than 100.

Accordingly, as a stabilizer, the amphiphilic RAFT agents stabilize the dispersed organic phase from coalescence through interfacial interactions, wherein the hydrophilic end orientates itself into the aqueous phase and the hydrophobic end orientates itself into the organic phase.

The dispersed organic phase may also be stabilized by other stabilizers such as conventional surfactants or any other surface active agent. Those skilled in the art would appreciate the range of surfactants suitable for this purpose. Preferably, the dispersed organic phase is stabilized by only the amphiphilic RAFT agent.

During polymerization the dispersed organic phase will typically consist of polymer and the one of more ethylenically unsaturated monomers. However, other components such as an organic solvent or seed particles may also be present in the organic phase. Depending on the nature of the polymerisation, initiator or components thereof may also be present in the organic phase.

The use of seed particles in conventional emulsion polymerisation is a well established technique. Typically such particles are in the form of polymer particles and they are selected such that they have the ability to swell in the monomers used. A person skilled in the art would readily appreciate criteria for consideration in selecting suitable seed particles for a given reaction system.

Dispersion of the organic phase in the continuous aqueous phase is usually achieved by agitating the mixture, for example by some shearing means. Processes for the formation of dispersion and the role of shear in conventional emulsion, mini-emulsion and suspension polymerisation techniques are readily appreciated by those skilled in the art. In accordance with the method of the present invention, ethylenically unsaturated monomers are polymerised under the control of the amphiphilic RAFT agent to form the aqueous dispersion of polymer particles.

The polymerisation will usually require initiation from a source of free radicals. The source of initiating radicals can be provided by any suitable method of generating free radicals, such as the thermally induced homolytic scission of suitable compound(s) (thermal initiators such as peroxides, peroxyesters, or azo compounds), the spontaneous generation from monomers (e.g. styrene), redox initiating systems, photochemical initiating systems or high energy radiation such as electron beam, X- or gamma-radiation. The initiating system is chosen such that under the reaction conditions there is no substantial adverse interaction of the initiator or the initiating radicals with the amphiphilic RAFT agent under the conditions of the reaction. The initiator ideally should also have the requisite solubility in the reaction medium.

Thermal initiators are chosen to have an appropriate half life at the temperature of polymerisation. These initiators can include one or more of the following compounds:

2,2'-azobis(isobutyronitrile), 2,2'-azobis(2-cyanobutane), dimethyl 2,2'-azobis(isobutyrate), 4,4'-azobis(4-cyanovaleric acid), 1,1'-azobis(cyclohexanecarbonitrile), 2-(t-butylazo)-2-cyanopropane, 2,2'-azobis{2-methyl-N-[1,1-bis(hydroxymethyl)-2-hydroxyethyl]propionamide}, 2,2'-azobis[2-methyl-N-(2-hydroxyethyl)propionamide], 2,2'-azobis(N,N'-dimethyleneisobutyramidine)dihydrochloride, 2,2'- azobis(2-amidinopropane) dihydrochloride, 2,2'-azobis(N,N'-dimethyleneisobutyramidine), 2,2'-azobis{2-methyl-N-[1,1-bis(hydroxymethyl)-2-hydroxyethyl]propionamide}, 2,2'-azobis {2-methyl-N-[1,1-bis(hydroxymethyl)-2-ethyl]propionamide}, 2,2'-azobis [2-methyl-N-(2-hydroxyethyl)propionamide], 2,2'-azobis(isobutyramide)dihydrate, 2,2'-azobis(2,2,4-trimethylpentane), 2,2'-azobis(2-methylpropane), t-butyl peroxyacetate, t-butyl peroxybenzoate, t-butyl peroxyneodecanoate, t-butylperoxy isobutyrate, t-amyl peroxypivalate, t-butyl peroxypivalate, diisopropyl peroxydicarbonate, dicyclohexyl peroxydicarbonate, dicumyl peroxide, dibenzoyl peroxide, dilauroyl peroxide, potassium peroxydisulfate, ammonium peroxydisulfate, di-t-butyl hyponitrite, dicumyl hyponitrite. This list is not exhaustive.

Photochemical initiator systems are chosen to have the requisite solubility in the reaction medium and have an appropriate quantum yield for radical production under the conditions of the polymerisation. Examples include benzoin derivatives, benzophenone, acyl phosphine oxides, and photo-redox systems.

Redox initiator systems are chosen to have the requisite solubility in the reaction medium and have an appropriate rate of radical production under the conditions of the polymerisation; these initiating systems can include, but are not limited to, combinations of the following oxidants and reductants:

oxidants: potassium, peroxydisulfate, hydrogen peroxide, t-butyl hydroperoxide.

reductants: iron (II), titanium (III), potassium thiosulfite, potassium bisulfite.

Other suitable initiating systems are described in recent texts. See, for example, Moad and Solomon "the Chemistry of Free Radical Polymerisation", Pergamon, London, 1995, pp 53-95.

Preferred initiating systems for conventional and miniemulsion processes are those which are appreciably water soluble. Suitable water soluble initiators include, but are not limited to, 4,4-azobis(cyanovaleric acid), 2,2'-azobis{2-methyl-N-[1,1-bis(hydroxymethyl)-2-hydroxyethyl]propionamide}, 2,2'-azobis[2-methyl-N-(2-hydroxyethyl)propionamide], 2,2'-azobis(N,N'-dimethyleneisobutyramidine), 2,2'-azobis(N,N'-dimethyleneisobutyramidine)dihydrochloride, 2,2'-azobis(2-amidinopropane) dihydrochloride, 2,2'-azobis{2-methyl-N-[1,1-bis(hydroxymethyl)-2-ethyl]propionamide}, 2,2'-azobis[2-methyl-N-(2-hydroxyethyl)propionamide], 2,2'-azobis(isobutyramide) dihydrate, and derivatives thereof.

Preferred initiating systems for suspension polymerization are those which are appreciably soluble in the monomer to be polymerized. Suitable monomer soluble initiators may vary depending on the polarity of the monomer, but typically would include oil soluble initiators such as azo compounds exemplified by the well known material 2,2'-azobisisobutyronitrile. The other class of readily available compounds are the acyl peroxide class such as acetyl and benzoyl peroxide as well as alkyl peroxides such as cumyl and t-butyl peroxides. Hydroperoxides such as t-butyl and cumyl hydroperoxides are also widely used. A convenient method of initiation applicable to suspension processes is redox initiation where radical production occurs at more moderate temperatures. This can aid in maintaining stability of the polymer particles from heat induced aggregation processes.

The aqueous phase in a given polymerization process may also contain other additives, for example additives to regulate pH.

The method of the present invention may be applied in many forms of emulsion polymerisation, for example conventional emulsion polymerisation, miniemulsion polymerisation, seed emulsion polymerisation and suspension polymerization. When the method is applied in such processes, presently accepted polymerisation mechanisms for such processes are believed to operate. However, processes employing the method of the present invention are distinguished by an amphiphilic RAFT agent acting as a stabilizer, and polymerisation being under the control of the amphiphilic RAFT agent.

Accordingly, when the method of the present invention is applied in a conventional emulsion polymerisation, the amphiphilic RAFT agents are present when polymerisation is initiated, and grow to become micelles which are non-labile and form particles. By this process, the amphiphilic RAFT agent is located at the reaction loci during the initial stages of polymerisation. In particular, the active hydrophobic RAFT portion is orientated towards the reaction loci and can effectively gain control over the free radical process.

It is an important feature of the method of the present invention that the amphiphilic RAFT agent gain control over the polymerisation, ie that the polymerisation of monomers proceed under a RAFT mediated free radical process. In order to ensure that the polymerisation proceeds under the control of the amphiphilic RAFT agent, it is preferred that the number of RAFT species is greater than the sum of initiating radicals reaching the locus of polymerisation produced through the course of the reaction so as to achieve the desired molecular weight characteristics of the final polymer. In general the total number of initiating radicals that enter the particles should be less than the number of amphiphilic RAFT agents present in the system. Preferably the total number of initiating radicals is less than 50 percent, more preferably less than 20 percent, of the number of amphiphilic RAFT agents present.

In accordance with the method of the present invention, after polymerisation has been initiated, and the reaction is proceeding under the control of the amphiphilic RAFT agent, polymerisation can be maintained through insertion of ethylenically unsaturated monomers at the living end of the agent. The composition and architecture of resulting polymer particles may be tailored through the selection and controlled addition of monomer.

A wide range of ethylenically unsaturated monomers may be used in accordance with the method of the present invention. Suitable monomers are those which can be polymerised by a free radical process. The monomers should also be capable of being polymerised with other monomers. The factors which determine copolymerisability of various monomers are well documented in the art. For example, see: Greenlee, R. Z., in Polymer Handbook 3$^{rd}$ Edition (Brandup, J., and Immergut. E. H. Eds) Wiley: New York, 1989 p II/53. Such monomers include those with the general formula (14):

(14)

where U and W are independently selected from the group consisting of —$CO_2H$, —$CO_2R^2$, —$COR^2$, —$CSR^2$, —$CSOR^2$, —$COSR^2$, —$CONH_2$, —$CONHR^2$, —$CONR^2_2$, hydrogen, halogen and optionally substituted $C_1$-$C_4$ alkyl wherein the substituents are independently selected from the group consisting of hydroxy, —$CO_2H$, —$CO_2R^1$, —$COR^2$, —$CSR^2$, —$CSOR^2$, —$COSR^2$, —CN, —$CONH_2$, —$CONHR^2$, —$CONR^2{}_2$, —$OR^2$, —$SR^2$, —$O_2CR^2$, —$SCOR^2$, and —$OCSR^2$; and V is selected from the group consisting of hydrogen, $R^2$, —$CO_2H$, —$CO_2R^2$, —$COR^2$, —$CSR^2$, —$CSOR^2$, —$COSR^2$, —$CONH_2$, —$CONHR^2$, —$CONR^2{}_2$, —$OR^2$, —$SR^2$, —$O_2CR^2$, —$SCOR^2$, and —$OCSR^2$;

where $R^2$ is selected from the group consisting of optionally substituted $C_1$-$C_{18}$ alkyl, optionally substituted $C_2$-$C_{18}$ alkenyl, optionally substituted aryl, optionally substituted heteroaryl, optionally substituted carbocyclyl, optionally substituted heterocyclyl, optionally substituted aralkyl, optionally substituted heteroarylalkyl, optionally substituted alkaryl, optionally substituted alkylheteroaryl and polymer chains wherein the substituents are independently selected from the group consisting of alkyleneoxidyl (epoxy), hydroxy, alkoxy, acyl, acyloxy, formyl, alkylcarbonyl, carboxy, sulfonic acid, alkoxy- or aryloxy-carbonyl, isocyanato, cyano, silyl, halo, amino, including salts and derivatives thereof. Preferred polymer chains include, but are not limited to, polyalkylene oxide, polyarylene ether and polyalkylene ether.

Examples of monomers include, but are not limited to, maleic anhydride, N-alkylmaleimide, N-arylmaleimide, dialkyl fumarate and cyclopolymerisable monomers, acrylate and methacrylate esters, acrylic and methacrylic acid, styrene, acrylamide, methacrylamide, and methacrylonitrile, mixtures of these monomers, and mixtures of these monomers with other monomers. As one skilled in the art would recognise, the choice of comonomers is determined by their steric and electronic properties. The factors which determine copolymerisability of various monomers are well documented in the art. For example, see: Greenlee, R Z. in Polymer Handbook $3^{rd}$ Edition (Brandup, J., and Immergut, E. H Eds.) Wiley: New York. 1989 pII/53.

Specific examples of useful ethylenically unsaturated monomers include the following: methyl methacrylate, ethyl methacrylate, propyl methacrylate (all isomers), butyl methacrylate (all isomers), 2-ethylhexyl methacrylate, isobornyl methacrylate, methacrylic acid, benzyl methacrylate, phenyl methacrylate, methacrylonitrile, alpha-methylstyrene, methyl acrylate, ethyl acrylate, propyl acrylate (all isomers), butyl acrylate (all isomers), 2-ethylhexyl acrylate, isobornyl acrylate, acrylic acid, benzyl acrylate, phenyl acrylate, acrylonitrile, styrene, functional methacrylates, acrylates and styrenes selected from glycidyl methacrylate, 2-hydroxyethyl methacrylate, hydroxypropyl methacrylate (all isomers), hydroxybutyl methacrylate (all isomers), N,N-dimethylaminoethyl methacrylate, N,N-diethylaminoethyl methacrylate, triethyleneglycol methacrylate, itaconic anhydride, itaconic acid, glycidyl acrylate, 2-hydroxyethyl acrylate, hydroxypropyl acrylate (all isomers), hydroxybutyl acrylate (all isomers), N,N-dimethylaminoethyl acrylate, N,N-diethylaminoethyl acrylate, triethyleneglycol acrylate, methacrylamide, N-methylacrylamide, N,N-dimethylacrylamide, N-tert-butylmethacrylamide, N-n-butylmethacrylamide, N-methylolmethacrylamide, N-ethylolmethacrylamide, N-tert-butylacrylamide, N-n-butylacrylamide, N-methylolacrylamide, N-ethylolacrylamide, vinyl benzoic acid (all isomers), diethylamino styrene (all isomers), alpha-methylvinyl benzoic acid (all isomers), diethylamino alpha-methylstyrene (all isomers), p-vinylbenzene sulfonic acid, p-vinylbenzene sulfonic sodium salt, trimethoxysilylpropyl methacrylate, triethoxysilylpropyl methacrylate, tributoxysilylpropyl methacrylate, dimethoxymethylsilylpropyl methacrylate, diethoxymethylsilylpropyl methacrylate, dibutoxymethylsilylpropyl methacrylate, diisopropoxymethylsilylpropyl methacrylate, dimethoxysilylpropyl methacrylate, diethoxysilylpropyl methacrylate, dibutoxysilylpropyl methacrylate, diisopropoxysilylpropyl methacrylate, trimethoxysilylpropyl acrylate, triethoxysilylpropyl acrylate, tributoxysilylpropylacrylate, dimethoxymethylsilylpropyl acrylate, diethoxymethylsilylpropyl acrylate, dibutoxymethylsilylpropyl acrylate, diisopropoxymethylsilylpropyl acrylate, dimethoxysilylpropyl acrylate, diethoxysilylpropyl acrylate, dibutoxysilylpropyl acrylate, diisopropoxysilylpropyl acrylate, vinyl acetate, vinyl butyrate, vinyl benzoate, vinyl chloride, vinyl fluoride, vinyl bromide, maleic anhydride, N-phenylmaleimide, N-butylmaleimide, N-vinylpyrrolidone, N-vinylcarbazole, butadiene, ethylene and chloroprene. This list is not exhaustive.

As applied in a conventional emulsion polymerisation, miniemulsion polymerisation and suspension polymerisation, the method of the present invention may be operated in batch, semi-continuous or continuous modes. Preferably, conventional emulsion polymerisation is operated in semi-continuous or continuous modes, and miniemulsion polymerisation and suspension polymerisation are operated in batch modes.

Semi-continuous and continuous modes of operation offer superior control of polymer architecture together with control over the polymer polydispersity. According to these modes of operation, monomer may be added gradually or in stages thereby enabling different monomers and other additives to be introduced during the course of the reaction. At a high solid content, large polymer particles may not be adequately stabilized. In this case, amphiphilic RAFT agent may also be added to the reaction with the monomer in order to replenish the surface of the particle with stabilizing moieties. Accordingly, the resulting aqueous dispersion of polymer particles will typically be more stable due to extra amphiphilic RAFT reagent acting to provide a greater stabilizing effect per polymer particle.

As applied in a conventional emulsion polymerisation, the method of the present invention is preferably operated in semi-continuous or continuous modes. A preferred method of carrying out such modes comprises adding a selected water soluble amphiphilic RAFT agent to a reaction vessel, together with a thermal initiator and water. Other reagents can also be added if required, for example buffers to regulate pH. Typically, all reagents used are essentially free from dissolved oxygen and the reaction solution is purged with an inert gas, such as nitrogen, prior to initiating the polymerisation. The solution temperature is then increased so that the initiator undergoes thermally induced homolytic scission. Monomer is then added and polymerisation can proceed under the control of the amphiphilic RAFT agent. The addition of monomer at this stage is maintained at a rate to avoid reservoir monomer droplets from forming, and is continued at such a rate until such time as sufficient monomer has been added to render the amphiphilic RAFT agent essentially water insoluble. At this point in time it is believed that non-labile micelles form. Further monomer, which may be the same or different, is then added at a greater rate either continually or in stages until the desired degree of polymerisation has occurred, preferably to give a latex having a solids content near 50%. Additional amphiphilic RAFT agent can be added during the course of the polymerisation, however it is preferable to adjust the rate of monomer addition as previously described.

Technical variations of the above preferred semi-continuous or continuous modes are also contemplated. For example, the polymerisation might initially be conducted without the use of an amphiphilic RAFT agent, for example using conventional surfactants and conducting the polymerisation by classical free radical polymerisation. At some point during the reaction water soluble amphiphilic RAFT agent is introduced. The added RAFT agent will associate itself with a growing polymer particle, and at this stage it is preferred that the rate of monomer addition is adjusted as previously described. Through the polymerised addition of monomer to the amphiphilic RAFT agent, the agent will become anchored to the growing particle to thereby act as a stabilizer. At this stage, the added amphiphilic RAFT agents have become non labile and the rate of monomer addition may be increased. The progress and the nature of the subsequent polymerisation will depend on the amount of amphiphilic RAFT agent added and when it is added. In this case, the resulting reaction system would contain both conventional surfactant and amphiphilic RAFT agent as stabilizers, where the amphiphilic RAFT agent has become firmly attached to the surface of growing particles.

As an alternatively to the above process, the polymerisation may initially be conducted under the control of an amphiphilic RAFT agent then allowed to proceed by a classical free radical process. In this case, polymerisation under RAFT control may be continued so as to provide a particular composition and or architectural effect, ie polymerising selected monomers to be located at the surface of the particle. Having achieved this effect, subsequent polymerisation may then proceed under a classical free radical process.

Where the method of the present invention is applied during initial stages of a conventional emulsion polymerisation, and no other surfactant species are present, as previously described it is preferable that the rate of addition of monomer is less than the rate of polymerisation. Under these conditions, stabilized propagating polymer particles have time to form and react with added monomer at a rate sufficient to avoid formation of non-stabilized monomer droplets. The formation of non-stabilized monomer droplets at this early stage in the reaction can lead to coagulum formation and a higher polydispersity of the polymer particles formed through entry of a propagating radical into the monomer droplet. Non-stabilized monomer droplets may also envelop small growing polymer particles. As the rate of reaction proceeds and the amphiphilic RAFT agent becomes non-labile, the problems associated with non-stabilized monomer droplet formation become less significant. In the case of batch emulsion polymerisations, it is preferable that sufficient amphiphilic RAFT agent is used to stabilize substantially all of the monomer present. If desired, other surfactant species may be added to any mode of performing an emulsion polymerisation in order to avoid the formation of non-stabilized monomer droplets.

As previously mentioned the method of the present invention may be applied to many forms of emulsion polymerisation techniques. From the preceding discussion of the method, one skilled in the art should readily appreciate how the method can be applied to such techniques.

Alternative modes of performing conventional emulsion polymerisation, such as miniemulsion or seed emulsion techniques, have recently been shown to alleviate problems associated with the diffusion of RAFT agents. However, both techniques employ conventional surfactants, and dispersions prepared thereby are subject to the aforementioned surfactant migration problems. Furthermore, both techniques require co-surfactant stabilizers and other additives which introduce unwanted components into the polymerising mixture and compromise the properties of the finished product to a point where the potential benefits of the RAFT process cannot be demonstrated.

By applying the method of the present invention to a miniemulsion polymerisation, no additional surfactant, other than the amphiphilic RAFT agent, is required to establish a stable latex. Preferably, the hydrophobic portion of the amphiphilic RAFT agent used in such a polymerisation is sufficiently hydrophobic to render the amphiphilic RAFT agent essentially insoluble in the continuous phase. Under these conditions there is substantially no labile amphiphilic RAFT agent in the continuous phase to stabilize nucleation of new particles.

A preferred method of performing a miniemulsion in accordance with the method of the present invention comprises first preparing a water insoluble amphiphilic RAFT agent, and dissolving it in the hydrophobic monomer(s) to be polymerised. If the hydrophobic portion of the water insoluble amphiphilic RAFT agent to be used is derived from the same monomers as those to be used in preparing the final latex product, the water insoluble amphiphilic RAFT agent can be advantageously prepared by bulk polymerisation in the monomers that will ultimately form the dispersed organic phase of the miniemulsion. The water insoluble amphiphilic RAFT agent/monomer solution is then emulsified in waster using appropriate mechanical means well known to those skilled in the art. Appropriate free radical initiator(s) are then added to the system and polymerisation proceeds in a manner similar to that of a conventional miniemulsion except that the polymerisation proceeds under the control of the amphiphilic RAFT agent. To a large extent, provided that the amphiphilic RAFT agent is insoluble in water and emulsification is sufficiently energetic, the particle size of the final product is controlled by the amount of amphiphilic RAFT agent initially present in the reaction. Advantageously, not only does the amphiphilic RAFT agent act to stabilize the miniemulsion but the growing hydrophobic tails can afford substantial protection against the well known process of emulsion destabilization by diffusion of monomers from small to large emulsion droplets, an effect known as Ostwald ripening.

In many respects, the application of the method of the present invention in suspension polymerisation is similar to the application in miniemulsion. Suspension polymerisation is traditionally used to produce much larger polymer particles than either emulsion polymerisation or miniemulsion polymerisation. Such particles may also be cross linked and therefore not film forming. Suspension polymer particles are usually formed by first preparing a dispersion comprising a continuous aqueous phase and a dispersed organic phase comprising monomer. Polymerisation of the monomer then results in the formation of an aqueous dispersion of polymer particles of the desired size. If desired, the polymer particles can be separated from the aqueous medium using known techniques, and collected As mentioned for miniemulsion polymerisation, suspension polymerisations performed in accordance with the present invention are preferably conducted with water insoluble amphiphilic RAFT agents. Preferably, the water insoluble RAFT agent is soluble in the dispersed organic phase. In the case where the amphiphilic RAPT agent is not soluble in either the water or organic phases, significantly more shear must be used in forming the dispersed organic phase in order to distribute the amphiphilic RAFT agent at the interface between the two phases. Preferably, the initiator used would be soluble in the monomer being polymerised.

The method of the present invention, utilising water soluble amphiphilic RAFT agents, can also be used to significantly simplify the current practice of using conventional RAFT agents in a seeded emulsion polymerisation. In this regard, monomer and surface active water soluble amphiphilic RAFT agents can be added to a latex seed such that subsequent polymerisation proceeds under RAFT control.

In formulations such as paints, adhesives, primers, fillers, and sealants the latex is usually the binding component. The formulation also typically comprises other formulation components such as coloured pigments, extenders, film forming aids and other additives, all present at different levels and in different combinations. In some formulations there may be blends of latexes present to achieve specific material properties or for special functions such as thickening. The material properties of formulation compound are responsible for delivering the level of performance required for the intended application.

The composition of the latex is crucial to the performance of any product. Conventional emulsion polymer processing allows for virtually unlimited variation of material properties derived from well established knowledge of how to formulate polymers using combinations of monomers to achieve hardness or elastomeric character. Conventional knowledge also allows for more subtle variation through the way monomers are added during the polymerisation so as to achieve special morphology within the structure of the polymer particles. During use, carrier water in the formulations will evaporate and the polymer particles will come together and physically entangle or coalesce to deliver the final material properties. The particulate nature of the polymer can be important. The particles have a surface and an interior that can be the same or different in polymer composition, and most applications require that particles coalesce completely so that all appearance of individual polymer particle character is lost. The extent to which conventional emulsion polymers meet this need is limited by the statistical nature of the free radical polymerisation process which gives a distribution in the size and composition of the polymer molecules. There is also an additional requirement to maintain colloidal stability of the particles once formed.

In other more specialised applications, polymer particles may be required to retain their particulate character. Such applications include crosslinked particles of controlled structure used as ion exchange resins, column packing materials for gel permeation chromatography and high value applications such as diagnostic kits in biomedical applications. For such applications, an advantage of the present invention is the control afforded to actual particle formation without the requirement for high levels of expensive surfactants or other stabilizers.

A notable feature of RAFT controlled polymerisation in the context forming aqueous dispersions of polymer particles for use in paint, primer, filler, sealant and adhesive applications is the ability to control the architecture of the polymer particles. Advantageously, the method of the present invention provides means to tailor the distribution of polymerised monomer throughout the polymer particle. In particular, the method provides means to polymerise specific or specialised monomers in strategic locations of the polymer particles.

Selective surface modification of a polymer particle may be achieved by initial polymerisation of a specific or specialised monomer. For example, highly hydrophobic monomers such as 2,2,2-trifluoroethyl methacrylate (TFEM) may be introduced at the initial stages of the polymerisation to provide a highly hydrophobic surface region concentrated in polymerised TFEM. Introducing TFEM to a polymer particle in this manner can promote stain resistance to a paint film when such particles are incorporated into a paint formulation. Alternatively, more polar monomers such as acrylamide, dimethyl amino ethyl methacrylate or ureido monomers may be polymerised initially or the hydrophilic portion of the amphiphilic RAFT agent to be used in the polymerisation may already comprise such monomers. Incorporation of such polar monomers at the surface of the polymer particles can assist in their adhesion to difficult surfaces when used in coating applications. In particular, as part of the hydrophilic end of the amphiphilic RAFT agent, the location of these monomers at the surface of the particles enables their properties as adhesion promoters to be maximised due to their ability to freely interact with a substrate during film formation. Typically, these specific or specialised monomers are added at relatively low levels, preferably at less than 10% of the total monomer content, more preferably less than 5% of the total monomer content.

As mentioned above, the nature of polymer particle formation can also allow the internal composition of the particle to be controlled. In particular, the composition of the internal portion of the particle can be varied from that of the surface composition to provide an internal core and an outer shell. In the simplest case, particles can be formed whereby a specific monomer is polymerised at one stage of the process and a different monomer is polymerised at a later stage to form a block copolymer. In this way, hard polymer particles with a soft film forming exterior and soft elastomeric particles with a hard non film forming skin can be formed. By the terms "hard" and "soft" polymer, it is meant polymers that are formed from monomers where the homopolymer glass transition temperature Tg is above and below room temperature, respectively. Hard monomers used in typical formulations include methyl methacrylate and styrene, whereas soft monomers are typically the esters of acrylic acid, such as the ethyl, butyl and 2-ethyl hexyl acrylates.

The preparation of the aqueous dispersion of polymer particles and the polymer particles prepared by the methods of the present invention utilises an amphiphilic RAFT agent as a stabilizer as well as a means for forming polymer. By virtue of the amphiphilic RAFT agent's participation in the polymerisation process, the stabilizing moiety becomes effectively anchored to the polymer particle. Accordingly, the method provides means to prepare aqueous dispersions of polymer particles and polymer particles that are not subject to the disadvantages of the presence of surfactant, in particular, surfactant migration. When used in combination with a conventional surfactant, the methods effectively reduce the amount of conventional surfactant required and thereby provides means to minimise the negative effects of the surfactant.

A common feature of commercial latex formulations is the use of low levels (1-5%) of acid monomers such as acrylic and methacrylic acids. Where such formulations are stabilized by conventional anionic surfactants alone, the use of acid monomers is essential to maintain stability of the dispersion. Accordingly, small quantities of the acid monomer are typically copolymerised with other monomers such as methyl methacrylate, styrene and acrylate esters to provide a final formulation with improved stability as measured by high shear and freeze thaw tests. The stability afforded to such dispersions results from ionisation of the acid units through the addition of base, this has the effect of increasing the charge on the particles surface and thereby improves stability. In the absence of the surfactant, stability could only be obtained by using much higher levels of acidic monomers or the introduction of surface charges derived from initiator residues or other mechanisms. The disadvantage of this approach is the reduced water sensitivity that results from the introduction of high levels of charged groups.

A surprising feature of this invention is the ability to maintain the colloidal stability of an anionically stabilized dispersion with levels of acid monomer far lower than can be achieved with conventional formulation practices. For example, a polymer latex can be produced to a solids content in excess of 50% where the level of copolymerised acid monomer is below 1% of the total polymer content.

The particle size characteristics of latexes which can be produced according to the present invention are also surprising in that a low level of acid monomer is capable of stabilizing small polymer particles. Polymer particles with a number average particle size of 40 nm are not easy to prepare by normal processing techniques and in general require the use of larger quantities of surfactant in order to stabilize the additional surface area associated with smaller particles. Particle size characteristics obtainable according to the present invention can only be achieved using prior art processes with surfactant loadings 10% or more on polymer solids or greater. For most applications where the polymer latex is used in its wet state, such as paints, primer, sealant and adhesives, this excess surfactant can adversely affect the properties of the film derived from the latex.

The selection of a specific amphiphilic RAFT agent for use in the methods of the present invention is particularly important. As mentioned above, the nature of their amphiphilic properties and their ability to stabilize the organic phase are two important aspects. It is also important that the amphiphilic RAFT agents be selected so that they have an ability to gain control over the polymerisation. Evidence of such control may be readily obtained by sampling an emulsion polymerisation reaction during processing and analyzing the resulting polymer by a suitable technique such as Gel Permeation Chromatography. Where there is control, the size of polymer molecules will grow in a linear fashion with conversion. Loss of control will be apparent with the appearance of additional peaks indicative of polymer formation by other mechanisms. The processes by which amphiphilic RAFT agents aggregate into reactive micelles and ultimately polymer particles can disrupt the RAFT reaction scheme. Control of a particular combination of monomers in solution or bulk polymerisation is no guarantee that a particular amphiphilic RAFT agent will be able to control an emulsion polymerisation reaction sufficiently. Good control is preferred in emulsion polymerisation reactions where the amphiphilic RAFT agent is chosen to be the sole means of stabilizing the growing particles. Without control, particle formation can be difficult depending on the combination of monomers chosen. If control is lost in the early stages of the reaction the result will be loss of particle stabilization and formation of polymer coagulum as the reaction proceeds. However, once particles have been formed, the maintenance of full control is a less serious issue and some deviation from ideal behaviour is generally tolerable.

In considering a suitable amphiphilic RAFT agent for use in accordance with the present invention, the group represented by $R^1$ in formula (4) may be selected such that it is either hydrophilic or hydrophobic in character. Due to $R^1$ being somewhat removed from the thiocarbonylthio group, its role in modifying the reactivity of the amphiphilic RAFT agent becomes limited as n increases. However, it is important that groups $-(X)_n-R^1$ and $-(A)_m-(B)_o-R^1$ (formula 13) are free radical leaving groups that are capable of reinitiating polymerisation.

The selection of Z is typically more important with respect to providing the amphiphilic RAFT agent with the ability to gain control over the polymerisation. In selecting a Z group for compounds of formula (4) it is important that such a group does not provide a leaving group that is a better leaving group in comparison with the $-(X)_n$, $-R^1$ or $-(A)_m-(B)_o-R^1$ (formula 13) groups. By this limitation, monomer insertion preferentially occurs between $-(X)_n-R^1$ or $-(A)_m-(B)_o-R^1$ and its nearest sulfur atom.

Amphiphilic RAFT agents of formula (4) may be prepared by a number of methods. Preferably they are prepared by polymerising ethylenically unsaturated monomers under the control of a RAFT agent having the following general formula (5).

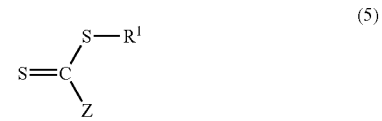

(5)

where Z and $R^1$ are as previously defined.

An important point to appreciate when considering the preparation of amphiphilic RAFT agents of general formula (4) from RAFT agents of general formula (5) is that the amphiphilic character associated with compounds of formula (4) is sufficient to stabilize the organic phase of the dispersion or to form a micelle type structure. Compounds of formula (5) may also have some amphiphilic character, however this will generally be insufficient to stabilize the organic phase of the dispersion or to form a micelle type structure. In order to achieve adequate stabilizing properties, in the context of compounds of formula (4), compounds of formula (5) are subsequently reacted with appropriate ethylenically unsaturated monomers. Having said this, when n=0 in connection with formula (4), it is to be understood that such a compound inherently possesses sufficient amphiphilic character to stabilize the organic phase of the emulsion or to form a micelle type structure. In this case, formula (4) is equivalent to formula (5), and $R^1$ and Z provide adequate hydrophilic and hydrophobic properties, in their own right to afford a suitable amphiphilic RAFT agent.

The ethylenically unsaturated monomers can be any such monomers that may be polymerised by a free radical process. In order to provide a RAFT agent with sufficient amphiphilic character to stabilize the organic phase or to form a micelle type structure, such monomers are chosen for their hydrophilic or hydrophobic qualities.

Examples of suitable hydrophilic ethylenically unsaturated monomers include, but are not limited to, acrylic acid, methacrylic acid, hydroxyethyl methacrylate, hydroxypropyl methacrylate, acrylamide and methacrylamide, hydroxyethyl acrylate, N-methylacrylamide, dimethylaminoethyl methacrylate or other monomers that give a water soluble polymer directly or by suitable post reaction.

Examples of suitable hydrophobic ethylenically unsaturated monomers include, but are not limited to, vinyl acetate, methyl methacrylate, methyl acrylate, styrene, alpha-methylstyrene, butyl acrylate, butyl methacrylate, amyl methacrylate, hexyl methacrylate, lauryl methacrylate, stearyl methacrylate, ethylhexyl methacrylate, crotyl methacrylate, cinnamyl methacrylate, oleyl methacrylate, ricinoleyl methacrylate, vinyl butyrate, vinyl tert-butyrate, vinyl stearate, vinyl laurate or other monomers that give a water insoluble polymer.

The polymerisation may be conducted in either an aqueous solution or an organic solvent, the choice of which is dictated primarily by the nature of the monomers to be polymerised. Polymerisation may also be conducted in the monomer itself.

The polymerisation reaction will usually require initiation from a source of radicals. Initiating systems previously described can also be applied in preparing the amphiphilic RAFT agents. However, in this case the initiator may also be soluble in the monomer or monomer mixture.

A preferred method for preparing an amphiphilic RAFT agent of formula (4) or (13) wherein $R^1$ is hydrophilic comprises first selecting a suitable RAFT agent. The selected RAFT agent is combined with a thermal initiator, solvent and hydrophilic monomer within a reaction vessel. Typically all reagents used are essentially free of dissolved oxygen and the reaction solution is purged of any remaining oxygen by way of an inert gas, such as nitrogen, prior to polymerisation. The reaction is subsequently initiated by increasing the temperature of the solution such that thermally induced homolytic scission of the initiator occurs. The polymerisation reaction then proceeds under control of the RAFT agent, thereby providing further hydrophilic character to the hydrophilic end of the RAFT agent through insertion of the hydrophilic monomer. For compounds of formula (4) in which Z is sufficiently hydrophobic, polymerisation of a second monomer may not be required. For compounds of formula (4) where Z is not sufficiently hydrophobic or for compounds of formula (13), upon exhaustion of the hydrophilic monomer, hydrophobic monomer may be added to the solution immediately, or at a later stage if the intermediate product is isolated, and the polymerisation continued under RAFT control to provide the block copolymer of formula (13). Where $R^1$ is intended to provide the hydrophobic properties to the RAFT agent, one skilled in the art will appreciate that the above method could be equally applied to prepare the "reverse" agent.

When compounds of formula (4) or (13) are prepared in accordance with the method described above and water is used as the solvent, upon reaching a point in the reaction where sufficient hydrophobic monomer has been polymerised onto the RAFT agent, the propagating RAFT agent is believed to self assemble to subsequently form non-labile micelles.

Surprisingly, the propagating RAFT agents which self assemble to form the non-labile micellular structures can maintain their activity allowing polymerisation to continue under RAFT control within the hydrophobic core of the micelle. By this process, polymerisation may be continued by supplying further monomer and additional reagents to prepare an aqueous dispersion of polymer particles, thus effectively preparing the amphiphilic RAFT agent in situ.

As a preferred mode of performing the method of the present invention, an amphiphilic RAFT agent is prepared in situ as described above. The resulting amphiphilic RAFT agent is then used in accordance with the method of the present invention to prepare an aqueous dispersion of polymer particles.

There are many technical variations to the way in which the method of the present invention may be performed. For example, a RAFT agent may first undergo partial polymerisation with particular monomers so as not to be substantially amphiphilic in character, for example to provide a RAFT agent that is substantially hydrophilic in character. This RAFT agent can then be isolated, and possibly stored, before use as an intermediate RAFT agent in subsequent preparation of the amphiphilic RAFT agent. Accordingly, a hydrophobic portion may be subsequently added to the hydrophilic RAFT agent in a secondary reaction or during the course of an emulsion polymerisation to provide the amphiphilic diblock structure of the compound of formula (13). Alternatively, it may also be desirable to add a number of hydrophobic monomer units to a substantially hydrophilic RAFT agent prior to its isolation as an intermediate RAFT agent. Depending on the polarity of such a RAFT agent, subsequent use of it in an emulsion polymerisation reaction or water based secondary reaction may require a water miscible cosolvent to assist it in becoming properly dispersed. Thus, a further preferred mode of performing the method of the present invention involves isolating an intermediate RAFT agent for subsequent use in the formation of an amphiphilic RAFT agent which may then be used in accordance with the method of the present invention.

As mentioned above, suitable RAFT agents for the preparation of the amphiphilic RAFT agents have the following general formula (5):

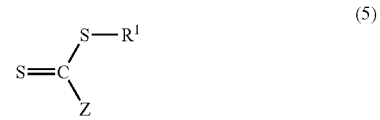

(5)

where $R^1$ and Z are as previously defined.

The effectiveness of a specific compound embraced by formula (5), as a RAFT agent, will depend on its transfer constant, which is determined by the nature of the $R^1$ and Z groups, the monomer and the prevailing reaction conditions. These considerations are discussed above in relation to the amphiphilic RAFT agents. With respect to the RAFT agents of formula (5), such considerations are essentially the same. In particular, as groups $R^1$ and Z are carried through to the amphiphilic RAFT agent, their selection is subject to similar considerations. However, due to closer proximity to the thiocarbonylthio group, the $R^1$ group plays a significant role in the effectiveness of a specific compound as a RAFT agent. In selecting both $R^1$ and Z groups for RAFT agents of formula (5), those agents resulting from the combination of particularly preferred $R^1$ and Z groups are also particularly preferred.

Most preferred RAFT agents include, but are not limited to, the following formulas (15-21):

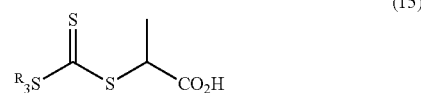

(15)

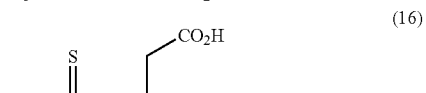

(16)

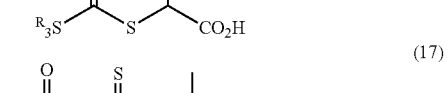

(17)

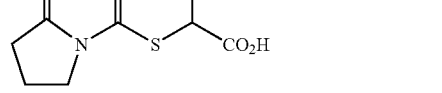

(18)

-continued

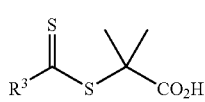
(19)

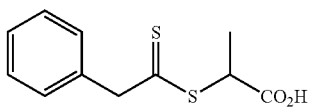
(20)

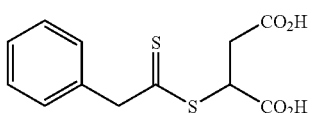
(21)

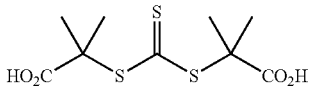
(24)

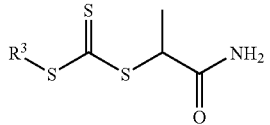
(25)

wherein $R^3$ is as previously defined.

When selecting a RAFT agent, it is preferable that it demonstrates hydrolytic stability under the conditions of emulsion polymerisation. In this regard, trithiocarbonyl RAFT agents are particularly preferred.

The dithiocarbonyl compound used in accordance with the fourth aspect of the invention may be a dithioester, a dithiocarbonate, a trithiocarbonate, a dithiocarbamate or the like. The important thing is that it has a Z—C(S)S$^\ominus$ component. The α,β-unsaturated compound may be any such compound capable of providing a RAFT agent following conjugate addition.

In a preferred embodiment the invention provides a method for the preparation of a RAFT agent comprising the conjugate addition of a compound of formula (I):

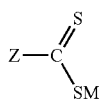
(I)

where M is hydrogen, an organic cation, or a metal and Z is any group that can promote sufficient reactivity of the thiocarbonyl group towards radical addition while not slowing the rate of fragmentation to the extent that there is unacceptable retardation of polymerisation, to the double bond of compound of formula (II):

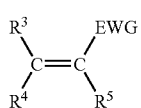
(II)

where EWG is an electron withdrawing group selected from —$CO_2H$, —$CO_2R^2$, —$COR^2$, —$CSR^2$, —$CSOR^2$, —$COSR^2$, —CN—$SO_2R^2$, —$SOR^2$, —$CONH_2$, —$CONHR^2$, —$CONR^2_2$;

$R^3$ is selected from H, $C_{1-6}$ alkyl, or together with either $R^4$ or EWG forms a —C(O)—O— group;

$R^4$ is selected from H, $C_{1-6}$ alkyl, aryl, heteroaryl, —$CO_2H$, —$CO_2R^2$, —$COR^2$, —$CSR^2$, —$CSOR^2$, —$COSR^2$, —CN—$SO_2R^2$, —$SOR^2$, —$CONH_2$, —$CONHR^2$, —$CONR^2_2$; and $R^5$ is selected from H, $C_{1-6}$ alkyl, aryl, heteroaryl;

wherein $R^2$ is selected from the group consisting of optionally substituted $C_1$-$C_{18}$ alkyl, optionally substituted $C_2$-$C_{18}$ alkenyl, optionally substituted aryl, optionally substituted heteroaryl, optionally substituted carbocyclyl, optionally substituted heterocyclyl, optionally substituted aralkyl, optionally substituted heteroarylalkyl, optionally substituted alkaryl, optionally substituted alkylheteroaryl and polymer chains wherein the substituents are independently selected from the group consisting of alkyleneoxidyl (epoxy), hydroxy, alkoxy, acyl, acyloxy, formyl, alkylcarbonyl, carboxy, sulfonic acid, alkoxy- or aryloxy-carbonyl, isocyanato, cyano, silyl, halo, amino, including salts and derivatives thereof.

Preferably at least one of $R^3$, $R^4$ and $R^5$ contributes to the reactivity of conjugate addition product to radical transfer.

Preferred Z group of formula (I) above include, optionally substituted with one or more hydrophilic substituents selected from —$CO_2H$, —$SO_3H$, —$OSO_3H$, —OH, —(COCH$_2$CHR)$_w$—OH, —$CONH_2$, —SOR and $SO_2R$, and salts thereof. Particularly preferred $R^1$ groups include, but are not limited to, —CH(CH$_3$)CO$_2$H, —CH(CO$_2$H)CH$_2$CO$_2$H, —C(CH$_3$)$_2$CO$_2$H. Preferred Z groups include, optionally substituted alkoxy, optionally substituted aryloxy, optionally substituted alkyl, optionally substituted aryl, optionally substituted heterocyclyl, optionally substituted arylalkyl, optionally substituted alkylthio, optionally substituted arylalkylthio, dialkoxy- or diaryloxy-phosphinyl [—P(=O)OR$^2_2$], dialkyl- or diaryl-phosphinyl [—P(=O)R$^2_2$], optionally substituted acylamino, optionally substituted acylimino, optionally substituted amino, $R^1$—(X)$_n$—S— and a polymer chain formed by any mechanism; wherein $R^1$; X and n are as defined above and $R^2$ is selected from the group consisting of optionally substituted $C_1$-$C_{18}$ alkyl, optionally substituted $C_2$-$C_{18}$ is alkenyl, optionally substituted aryl, optionally substituted heterocyclyl, optionally substituted aralkyl, optionally substituted alkaryl. Particularly preferred Z groups include, but are not limited to, —CH$_2$(C$_6$H$_5$), C$_1$-C$_{20}$alkyl, —N(CO)(CH$_2$)$_e$CH$_2$, where e is 2 to 4, and —SR$^3$, where R$^3$ is selected from C$_1$ to C$_{20}$ alkyl.

DETAILED DESCRIPTION OF THE INVENTION

The invention will now be described with reference to the following examples which illustrate some preferred embodiments of the invention. However, it is to be understood that the particularity of the following description is not to supersede the generality of the preceding description of the invention.

EXAMPLE 1

Synthesis of
2-[(2-phenylethanethioyl)sulfanyl]propanoic Acid
(20)

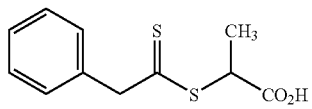

A solution of benzylmagnesium chloride in ether (1.0 M, 40 mL, 40 mmol) was added slowly with stirring to an ice-cooled solution of carbon disulfide (4.0 mL, 66 mmol) in dry tetrahydrofuran (40 mL) under nitrogen. After 30 min, 2-bromopropanoic acid (3.6 mL, 6.2 g, 40 mmol) was added and the reaction was stirred at ambient temperature. After 48 h, the mixture was poured into ethyl acetate (200 mL) and washed with water (3×100 mL), followed by saturated sodium chloride solution (100 mL). The organic layer was dried (magnesium sulfate) and evaporated. The remaining liquid was distilled (120°/0.13 Pa, Kugelrohr) to remove unreacted 2-bromopropanoic acid. The residue was then dissolved in ether (200 mL) and extracted with 5% sodium bicarbonate solution (4×50 mL). The combined aqueous extracts were washed with ether (100 mL), then acidified to pH<1 with 2 M hydrochloric acid. The resulting mixture was extracted with ethyl acetate (2×100 mL) and the combined organic extracts were washed with water (2×50 mL), saturated sodium chloride (50 mL) and then dried with magnesium sulfate. Evaporation of the solvent gave the title compound (20) as a red liquid (3.73 g, 39%) which slowly solidified on standing.

EXAMPLE 1a

Preparation of a poly(acrylic acid)-block-poly(butyl acrylate) Macro-RAFT Agent with Respective Degrees of Polymerization n≈5 and n≈20 Using 2-[(2-phenylethanethioyl)sulfanyl]propanoic Acid (20) from Example 1

A solution of 2-[(2-phenylethanethioyl)sulfanyl]propanoic acid (20) (0.416 g, 1.73 mmol), 4,4'-azobis(4-cyanopentanoic acid), (95 mg, 0.30 mmol) and acrylic acid (0.624 g, 8.78 mmol) in THF (5.0 g) in a 50 mL round bottomed flask was stirred magnetically and sparged with nitrogen for 15 min. The flask was then heated at 85° for 2 h. At the end of this period, butyl acrylate (4.50 g, 35 mmol) was added to the flask and heating was continued at 85° for a further 3 h. The resulting diblock copolymer showed molecular weight characteristics consistent with formation under RAFT control. The copolymer solution had 54.3% solids.

EXAMPLE 1b

Preparation of a poly(butyl acrylate-co-methyl methacrylate) Latex Using the Macro-RAFT Agent from Example 1a 4,4'-Azobis(4-cyanopentanoic acid), (25 mg, 0.08 mmol), diblock copolymer solution from Example 1a (5.96 g of solution; containing 3.23 g, 1.02 mmol of macro-RAFT agent), water (48.0 g) and sodium hydroxide (0.12 g, 3.0 mmol) were placed in a 100 mL round bottomed flask and stirred magnetically while being sparged with nitrogen for 15 min, then heated at 85° with continued stirring. After 15 min a mixture of methyl methacrylate (19.5 g, 0.195 mol) and butyl acrylate (19.5 g, 0.152 mol), was added in portions at 45 min intervals with the following weights added at each step: 4 g, 5 g, 6 g, 7 g, 8 g, 9 g. After the last addition, the reaction was held at 85° for a further 3 h and then allowed to cool. The latex was 45% solids and had a number average particle size of 40 nm (CHDF).

EXAMPLE 1c

Preparation of a poly(acrylic acid)-block-poly(butyl acrylate) Macro-RAFT Agent with Degree of Polymerization n≈20 for Both Blocks Using 2-[(2-phenylethanethioyl)sulfanyl]propanoic acid (20) from Example 1

A solution of 2-[(2-phenylethanethioyl)sulfanyl]propanoic acid (20) (0.563 g, 2.34 mmol), 4,4'-azobis(4-cyanopentanoic acid) (0.102 g, 0.32 mmol), and acrylic acid (3.40 g, 47.2 mmol) in THF (10.0 g) was stirred and deoxygenated by sparging with nitrogen for 20 min. The solution was then heated at 85° for 2 h, after which butyl acrylate (6.06 g, 47.0 mmol) was added. Heating was continued for a further 4 h to complete the polymerization.

EXAMPLE 1d

Preparation of a poly(butyl acrylate-co-methyl methacrylate) Latex Using the Macro-RAFT Agent from Example 1c The diblock copolymer solution from Example 1c (8.11 g of solution, containing 4.05 g, 0.95 mmol of macro-RAFT agent), 4,4'-azobis(4-cyanopentanoic acid) (0.25 g, 0.80 mmol), water (47.9 g) and sodium hydroxide (1.27 g, 31.8 mmol) were stirred while nitrogen was bubbled through the solution for 15 min. The mixture was then heated to 85°, and after allowing 15 min for equilibration, a mixture of methyl methacrylate (13 g, 0.13 mol) and butyl acrylate (13 g, 0.10 mol) was added in successive portions of 4 g, 4 g, 4 g, 4 g, 5 g, and 5 g at 1 h intervals. Samples were taken prior to each addition and the molecular weight of the polymer in the sample was determined by gel permeation chromatography (polystyrene standard). Peak molecular weight (polystyrene standard) is shown as a function of time in the table below, and its progressive increase shows the polymerisation is under RAFT control. The final latex had a solids content of 34%.

| Reaction time (h) | Peak molecular weight |
| --- | --- |
| Flask to temperature (t = 0) | 1,087 |
| 1 | 19,324 |
| 2 | 25,860 |
| 3 | 34,759 |
| 4 | 45,629 |
| 5 | 61,682 |

EXAMPLE 1e

Preparation of a Higher Solids Content poly(butyl acrylate-co-methyl methacrylate) Latex Using the Macro-RAFT Agent from Example 1c The diblock copolymer solution from Example 1c (10.0 g of solution, containing 1.2 mmol of macro-RAFT agent), 4,4'-azobis(4-cyanopentanoic acid) (25 mg, 0.089 mmol), water (48 mL) and sodium hydroxide (1.25 g, 31.3 mmol) were stirred magnetically while being sparged with nitrogen for 15 min, then heated at 85° with continued stirring. After 15 min a mixture of methyl methacrylate (22.5 g, 0.225 mol) and butyl acrylate (22.5 g, 0.176 mol) was added in successive portions of 5 g, 6 g, 7 g, 8 g, 9 g, and 10 g at 45 min intervals. The final latex had 42.1% solids. Particle sizing using transmission electron microscopy indicated a final particle diameter of less than 60 nm.

EXAMPLE 2

Synthesis of 2-[(2-phenylethanethioyl)sulfanyl]succinic Acid (21)

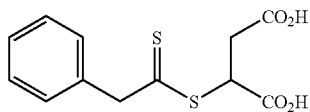

A solution of benzylmagnesium chloride in ether (1.0 M, 200 mL, 0.20 mol) was added to dry tetrahydrofuran (200 mL) under nitrogen. Carbon disulfide (20 mL, 25 g, 0.33 mol) was then added slowly with stirring. After 15 min, fumaric acid (23.2 g, 0.20 mol) was added and the ether was mostly removed by distillation. More tetrahydrofuran (100 mL) was added, and the solution was heated under reflux for 14 h. The reaction was cooled and poured into ether (1 L), then extracted with water (3×100 mL) followed by saturated sodium bicarbonate (5×200 mL). The bicarbonate extracts were combined and extracted with ether (2×100 mL), then acidified slowly to pH<1 with concentrated hydrochloric acid, and extracted with ethyl acetate (3×200 mL). The combined organic layers were washed with water (200 mL) and saturated sodium chloride (100 mL), and then evaporated. The crude mixture was crystallized by trituration with 50:50 ether/light petroleum (100 mL). The solid was collected and placed in water (150 mL) at 65° whereupon most of the solid dissolved. The mixture was then quickly cooled in an ice bath and the resulting crystals were collected and washed with cold water (3×33 mL). The solid was then dissolved in a mixture of water (150 mL), ethyl acetate (600 mL) and tetrahydrofuran (50 mL). The water was removed and the organic phase was washed with water (3×100 mL), saturated sodium chloride (100 mL), dried over magnesium sulfate, and evaporated to give the title compound (21) as a yellow solid (18.4 g, 33%).

EXAMPLE 2a

Preparation of a poly(acrylic acid) Macro-RAFT Agent with Degree of Polymerization n≈23 Using 2-[(2-phenylethanethioyl)sulfanyl]succinic acid (21) from Example 2

A solution of 2-[(2-phenylethanethioyl)sulfanyl]succinic acid (21) (700 mg, 2.46 mmol), 4,4'-azobis(4-cyanopentanoic acid) (40 mg, 0.14 mmol), and acrylic acid (4.0 mL, 58 mmol) in tetrahydrofuran (10 mL) was sparged with nitrogen then heated at 60° for 14 h. The solution was evaporated to dryness under reduced pressure to give poly(acrylic acid) with an average degree of polymerization n≈23 as shown by gel permeation chromatography (polystyrene standard).

EXAMPLE 2b

Preparation of a poly(butyl acrylate) Latex Using the Macro-RAFT Agent from Example 2a Poly(acrylic acid) macro-RAFT agent from Example 2a (1.2 g, 0.60 mmol) and triethylamine (0.55 mL, 4.0 mmol), were dissolved in water (40 mL) and sparged with nitrogen, then heated to 68° while being stirred magnetically. After 10 min, butyl acrylate (2.0 mL, 14 mmol), and 4,4'-azobis(4-cyanopentanoic acid) (50 mg, 0.18 mmol) were added and stirring was continued for 1 h. More 4,4'-azobis(4-cyanopentanoic acid) (10 mg, 0.035 mmol) was then added, and the addition of butyl acrylate (2.1 mL, 0.16 mol) was commenced at a rate of 0.25 mL/min. At the end of the addition the solids content of the latex was 34%, and the molecular weight characteristics were as expected for a controlled polymerization.

EXAMPLE 2c

Preparation of a poly(acrylic acid) Macro-RAFT Agent with Degree of Polymerization N≈15 Using 2-[(2-phenylethanethioyl)sulfanyl]succinic Acid (21) from Example 2

A solution of 2-[(2-phenylethanethioyl)sulfanyl]succinic acid (21) (3.12 g, 11.0 mmol), 4,4'-azobis(4-cyanopentanoic acid) (200 mg, 0.71 mmol), and acrylic acid (11.3 mL, 0.164 mmol) in tetrahydrofuran (50 mL) was sparged with nitrogen then heated at 68° for 9 h. The resulting solution was evaporated to dryness under reduced pressure to give poly(acrylic acid) with an average degree of polymerization n≈15 as shown by gel permeation chromatography (polystyrene standard).

EXAMPLE 2d

Preparation of a poly(butyl acrylate-co-styrene) Latex Using the Macro-RAFT Agent from Example 2c Poly(acrylic acid) macro-RAFT agent from Example 2c (350 mg, 0.26 mmol) was dissolved in water (10 mL), sparged with nitrogen, then stirred and heated to 68°. Triethylamine (0.31 mL, 2.2 mmol), and 4,4'-azobis(4-cyanopentanoic acid) (50 mg, 0.18 mmol) were added, then after 5 mins, a 1:1 mixture of styrene and butyl acrylate (2.0 mL) was added at a rate of 1.0 mL/min. When this addition was complete, more of the poly(acrylic acid) from Example 2c (300 mg, 0.22 mmol) and triethylamine (0.40 mL, 5.4 mmol) dissolved in water (2 mL) was added at a rate of 0.02 mL/min at the same time as a 1:1 mixture of styrene and butyl acrylate (12 mL) at a rate of 0.1 mL/min. Stirring and heating was continued for 2 h after the addition had been completed. The final latex had 48% solids and the molecular weight characteristics were as expected for a controlled polymerization.

EXAMPLE 2e

Preparation of a Fluorinated Macro-RAFT agent, poly(acrylic acid)-block-poly(butyl acrylate-co-trifluoroethyl methacrylate) with Respective Degrees of Polymerization n≈5 and n≈20, Using 2-[(2-phenylethanethioyl)sulfanyl]succinic acid (21) from Example 2

2-[(2-Phenylethanethioyl)sulfanyl]succinic acid (21) (0.995 g, 3.5 mmol) and initiator, 4,4'-azobis(4-cyanopentanoic acid), (196 mg, 0.70 mmol) were dissolved in tetrahydrofuran (30 g) in a 100 mL round bottom flask. Acrylic acid (1.26 g, 17.5 mmol) was then added, the flask was sealed with a rubber septum, and nitrogen was bubbled through the solution for 15 min. The flask was immersed in an oil bath at 80° for 2 h, after which a mixture of trifluoroethyl methacrylate (5.88 g, 35 mmol) and butyl acrylate (4.49 g, 35 mmol) was added dropwise into the reaction. After 4.5 h a small amount of extra initiator was added and heating was continued for a further 4 h. Infrared analysis showed that all the monomers had been consumed. The final solution was 29.1% solids.

EXAMPLE 2f

Preparation of a poly(butyl acrylate-co-methyl methacrylate) Latex Using the Fluorinated Macro-RAFT Agent from Example 2e 4,4'-Azobis(4-cyanopentanoic acid) (120 mg, 0.43 mmol), water (17.4 g), and 10% (w/w) sodium hydroxide solution (0.95 g, 2.4 mmol) in a 100 mL round bottom flask were stirred magnetically until the initiator had all dissolved. The diblock copolymer solution from Example 2e (1.53 g of solution, containing 0.45 g, 0.12 mmol macro-RAFT agent) was added with high speed stirring over 1 min and the resulting mixture was stirred for 10 min to achieve complete dissolution. The flask was then sealed with a rubber septum and the solution was stirred and sparged with nitrogen for 15 mins. The reaction was then immersed in a heating bath at 80° and allowed to equilibrate for 15 min. A mixture of methyl methacrylate (6.00 g, 60.0 mmol) and butyl acrylate (6.00 g, 46.9 mmol) was then added in portions from a syringe: an initial addition of 2.6 mL was followed after 30 min by eight further additions of 1.3 mL each at 30 min intervals. The final latex had a solids content of 39.2% and average particle size $D_n$=68.9 nm with polydispersity $D_w/D_n$=1.11 (CHDF).

EXAMPLE 3

Synthesis of 2-{[(butylsulfanyl)carbonothioyl]sulfanyl}propanoic Acid (15, $R^3$=$C_4H_9$)

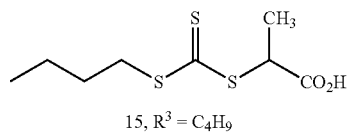

15, $R^3$ = $C_4H_9$

Acetone (700 mL) and tetrapropylammonium bromide (5.58 g, 21.0 mmol) were added with stirring to a solution of sodium hydroxide (10.5 g, 0.263 mol) in water (36 mL), followed by 1-butanethiol (23.7 g, 0.263 mol). After 20 min, carbon disulfide (17 mL, 21.7 g, 0.285 mol) was added and stirring was continued for 15 min, after which 2-bromopropanoic acid (40.14 g, 0.263 mol) was added. The reaction was stirred overnight, then acidified to pH<1 with 2 M hydrochloric acid (100 mL). The acetone was removed under reduced pressure and the remaining mixture was extracted with ether (400 mL). The extract was washed with water (2×100 mL), saturated sodium chloride solution (200 mL), dried (sodium sulfate), and evaporated. The oily residue was crystallized by the addition of ice (500 g), the crystals were collected by filtration and washed with water (5×100 mL) and then dried in a vacuum oven at room temperature. The resulting impure product was redissolved in ether (400 mL) and extracted with saturated sodium bicarbonate (5×150 mL). The combined aqueous extracts were acidified to pH<1 with concentrated hydrochloric acid and extracted with ether (400 mL). The organic extract was washed with saturated sodium chloride (200 mL), dried (sodium sulfate), and evaporated under reduced pressure. The residue was crystallized by the addition of ice (500 g) and the solid was collected and washed with water (5×1 50 mL), then dried in a vacuum oven to give the title compound (15, $R^3$=$C_4H_9$) as a yellow solid (39.0 g, 62%).

EXAMPLE 3a

Preparation of a poly(acrylic acid) Macro-RAFT Agent with Degree of Polymerization n≈5 Using 2-{[(butylsulfanyl)carbonothioyl]sulfanyl}propanoic Acid (15, $R^3$=$C_4H_9$) from Example 3

2-{[(Butylsulfanyl)carbonothioyl]sulfanyl}propanoic acid (15, R=$C_4H_9$) (3.30 g, 13.9 mmol), 4,4'-azobis(4-cyanopentanoic acid) (387 mg, 1.38 mmol), acrylic acid (5.01 g, 69.6 mmol) and sodium hydroxide (554 mg, 13.9 mmol) were dissolved in water (6.75 g) in a round bottom flask and capped with a rubber septum. Nitrogen was bubbled through the solution for five minutes, after which it was immersed in an oil bath at 60° for 2 hours. Electrospray Mass Spectrometry confirmed a degree of polymerization n≈5.

EXAMPLE 3b

Preparation of a poly(butyl acrylate) Latex Using the Macro-RAFT Agent from Example 3a The poly(acrylic acid) from Example 3a (0.585 g of solution, containing 0.304 g, 0.508 mmol of macro-RAFT agent), 4,4'-azobis(4-cyanopentanoic acid) (73 mg, 0.26 mmol), sodium hydroxide (83.4 mg, 2.09 mmol), and water (80.3 g) were added to a round bottom flask which was then sealed with a rubber septum. The solution was stirred magnetically and deoxygenated for 15 minutes with a stream of bubbled nitrogen. The flask was consisted of an oil bath at 60° and the addition of butyl acrylate was started. The addition consisted of an initial shot of 0.10 g, followed by a continuous feed at 1.00 g/h for 2 h, followed by 5.97 g/h for a further 3 h to give a total addition of 20.0 g (0.156 mol). The reaction was allowed to proceed for another hour after the cessation of monomer feed to allow the polymerisation to reach higher conversion. Molecular weight (polystyrene standard), solids, and particle size (CHDF) data are given in the Table following

| Reaction Time (min) | Solids Content | $\overline{M}_n$ (GPC) | $\overline{M}_w$ GPC) | Number Average Particle Diameter/nm (Polydispersity Index) |
|---|---|---|---|---|
| 30 | 0.79% | — | — | — |
| 60 | 0.70% | — | — | — |
| 90 | 1.27% | 2632 | 3334 | — |
| 120 | 2.05% | 5382 | 6063 | — |
| 150 | 3.03% | 7713 | 8936 | — |
| 180 | 3.80% | 10251 | 12326 | 43.1 (1.14) |
| 210 | 4.38% | 14202 | 16673 | 45.3 (1.22) |
| 240 | 6.54% | 20223 | 24740 | 50.6 (1.10) |
| 270 | 8.10% | 24216 | 31289 | 54.2 (1.10) |
| 300 | 10.04% | 29079 | 39240 | 56.9 (1.10) |
| 330 | 11.56% | 38212 | 53340 | 59.8 (1.10) |
| 360 | 13.33% | 46770 | 69817 | 60.3 (1.11) |

EXAMPLE 3c

Preparation of a poly(butyl acrylate) Latex Using a poly(acrylic acid) Macro-RAFT Agent Prepared According to the Description in Example 3a, and Potassium Persulfate as the Initiator A solution of poly(acrylic acid) macro-RAFT agent prepared according to the procedure described in Example 3a (0.601 g of solution, containing 0.316 g, 0.528 mmol of macro-RAFT agent), potassium persulfate (73 mg, 0.27 mmol), sodium hydroxide (83 mg, 2.1 mmol), and water (80.8 g) were placed in a round bottom flask which was then sealed with a rubber septum. The solution was swirled to disperse the RAFT agent, stirred magnetically while being deoxygenated with a stream of bubbled nitrogen. The flask was immersed in an oil bath at 60° and butyl acrylate addition was started. An initial addition of 0.10 g was followed by a continuous feed at 1.00 g/h for 2 h, then 5.97 g/h for a further 3 h to give a total addition of 20.0 g (156 mmol). Heating was continued for another hour after the end of the monomer feed to maximise conversion.

EXAMPLE 3d

Preparation of a poly(acrylic acid)-block-poly(butyl acrylate) Macro-RAFT Agent with Respective Degrees of Polymerization n≈5 and n≈20 using 2-{([(butylsulfanyl)carbonothioyl]sulfanyl}propanoic Acid (15, $R^3=C_4H_9$) from Example 3

A solution of 2-{[(butylsulfanyl)carbonothioyl]sulfanyl}propanoic Acid (15, $R=C_4H_9$) (1.13 g, 4.7 mmol), 4,4'-azobis(4-cyanopentanoic acid) (0.13 g, 0.47 mmol) and acrylic acid (1.72 g, 23.8 mmol) in dioxane (15 g) was prepared in a 50 mL round bottom flask. This solution was stirred magnetically and sparged with nitrogen for 5 min, then heated at 60° for 3 h. At the end of this period, butyl acrylate (12.04 g, 93.91 mmol) was added to the flask and heating was continued at 80° for a further 20 h. The resulting copolymer solution had 52.5% solids.

EXAMPLE 3e

Preparation of a poly(butyl acrylate) Latex by Miniemulsion Polymerization Using the Macro-RAFT Agent from Example 3d The poly(acrylic acid)-block-poly(butyl acrylate) macro-RAFT agent solution from Example 3d (7.60 g of solution; containing 3.99 g, 1.2 mmol of macro-RAFT agent) was mixed with butyl acrylate (24.5 g, 191 mmol) and water (46 g) in a 100 mL beaker and was vigorously stirred magnetically. Sodium hydroxide (0.25 g, 6.2 mmol) was then added to this mixture, forming a white emulsion. After stirring for 1 h, the emulsion was subjected to ultrasonication for 7 minutes using a Vibra-Cell Ultrasonic Processor (Sonics and Materials, Inc.) standard probe at 30% amplitude, resulting in a white miniemulsion. The miniemulsion was transferred to a 100 mL round bottom flask containing 4,4'-azobis(4-cyanopentanoic acid) (28 mg, 0.10 mmol). The flask was sealed with a with a rubber septum and the miniemulsion was stirred magnetically and sparged with nitrogen for 10 min, then heated at 60° in an oil bath for 3 h. At the end of the heating period, the latex had 36% solids and an average particle size of 88 nm (HPPS).

EXAMPLE 3f

Preparation of a poly(acrylic acid)-block-polystyrene Macro-RAFT Agent with Respective Degrees of Polymerization n≈5 and n 20 Using 2-{[(butylsulfanyl)carbonothioyl]sulfanyl}propanoic acid (15, $R^3=C_4H_9$) from Example 3

2-{[(Butylsulfanyl)carbonothioyl]sulfanyl}propanoic acid (15, $R^3=C_4H_9$) (0.666 g, 2.8 mmol), 4,4'-azobis(4-cyanopentanoic acid) (80 mg, 0.28 mmol) and acrylic acid (1.02 g, 14.2 mmol) were dissolved in dioxane (7.5 g) in a 25 mL round bottom flask. This solution was stirred magnetically and sparged with nitrogen for 5 minutes, then heated at 60° for 3 h. At the end of this period, styrene (5.9 g, 57 mmol) was added to the flask and heating was continued at 80° for a further 20 h. The resulting copolymer solution had 45% solids.

EXAMPLE 3g

Preparation of a Polystyrene Latex by Miniemulsion Polymerization Using the Macro-RAFT Agent from Example 3f The poly(acrylic acid)-block-polystyrene macro-RAFT agent solution from Example 3h (4.7 g of solution, containing 2.1 g, 0.86 mmol of macro-RAFT agent) was mixed with styrene (5.04 g, 48 mmol) and water (45.5 g) in a 100 mL beaker and was vigorously stirred magnetically. Sodium hydroxide (0.17 g, 4.3 mmol) was added to this mixture to form a white emulsion. After stirring for 1 h, the emulsion was subjected to ultrasonication for 10 minutes using Vibra-Cell Ultrasonic Processor (Sonics and Materials, Inc.) standard probe at 30% amplitude, resulting in a white miniemulsion. The miniemulsion was transferred to a 50 mL round bottom flask containing 4,4'-azobis(4-cyanopentanoic acid) (15 mg, 0.052 mmol), the flask was sealed with a rubber septum, and the solution was sparged with nitrogen for 10 minutes, stirred magnetically, then heated in an oil bath at 60° for 3 h. Polymer molecular weight distributions were determined by gel permeation chromatography (GPC, Shimadzu with Waters HR4, HR3 and HR2 columns, 5% acetic acid in tetrahydrofuran eluent, polystyrene standards, refractive index detection and Polymer Laboratories Cirrus™ software) as a function of conversion. The average molecular weight increased almost linearly while the polydispersity of the polymer was always below 1.2, indicating the styrene polymerisation was under the control of the macro-RAFT agent during the reaction. At the end of reaction period the solids content was 12% and the average particle size was 98 nm.

EXAMPLE 3h

Preparation of a Latex from Styrene Copolymerized with an Unsaturated Polyester by Miniemulsion Polymerization Using the Macro-RAFT Agent from Example 3f The unsaturated polyester used herein is a proprietary material (Dulux Australia) made from maleic anhydride, phthalic anhydride, and propylene glycol, and supplied as a 66% solution in styrene.

The poly(acrylic acid)-block-polystyrene macro-RAFT agent solution from Example 3f (4.77 g of solution; containing 2.15 g, 0.86 mmol of macro-RAFT agent) was mixed with styrene (5.4 g, 52 mmol), unsaturated polyester resin (4.6 g; 66% reactive polyester in styrene) and water (40 g) in a 100 mL beaker and was vigorously stirred magnetically. Sodium hydroxide (0.18 g, 4.5 mmol) was added to this mixture to form a white emulsion. After 1 h of stirring, the emulsion was subjected to ultrasonication for 10 minutes using Vibra-Cell Ultrasonic Processor (Sonics and Materials, Inc.) standard probe at 30% amplitude, resulting in a white miniemulsion. The miniemulsion was transferred to a 50 mL round bottom flask containing 4,4'-azobis(4-cyanopentanoic acid) (20 mg, 0.070 mmol). The flask was sealed with a rubber septum and stirred magnetically while nitrogen was bubbled through the emulsion for 10 min. The flask was then immersed in an oil bath at 60° for 3 h. At the end of this period, heating was stopped and another portion of 4.4'-azobis(4-cyanopentanoic acid) (12 mg, 0.043 mmol) was added to the flask. The solution was sparged with nitrogen for a further 5 min, the temperature was raised to 70°, and heating was resumed for a further 3 h. The final latex was 23% solids and had an average particle size of 137 nm (HPPS).

EXAMPLE 3i

Preparation of a poly(butyl acrylate)-block-polystyrene Core-Shell Emulsion Polymer Using a poly(acrylic Acid) Macro-RAFT Agent Prepared According to the Description in Example 3a A solution of poly(acrylic acid) macro-RAFT agent prepared according to the procedure described in Example 3a (0.639 g of solution; containing 0.350 g, 0.59 mmol of macro-RAFT agent), 4,4'-azobis(4-cyanopentanoic acid) (0.081 g, 0.29 mmol) and sodium hydroxide (0.094 g, 2.4 mmol) was dissolved in water (80 g) in a 100 mL round bottom flask. The flask was sealed with a rubber septum, the solution was stirred magnetically and sparged with nitrogen for 10 min, and then heated to 600. Deoxygenated butyl acrylate (10 g, 78 mmol), was then added by a syringe pump over 3.5 h in three stages as follows: an initial dose of 0.1 g was followed by then 2.0 g over 2 h, and finally 7.9 g over 1.5 h. Heating was continued for a further 1 h after the butyl acrylate addition was finished. At the end of this period, deoxygenated styrene (10 g, 96 mmol) was added to the reaction, the temperature was raised to 75°, and heating was continued for a further 20 h. The resulting latex had solids of 21% and the average particle size, determined by TEM and HPPS, was 50 nm. The core-shell nature of the latex particles was shown by electron microscopy.

EXAMPLE 3j

Preparation of a poly(butyl acrylate) Latex by a 2-Stage Process Involving Miniemulsion Polymerization Followed by a Slow Butyl Acrylate Addition, Using the Macro-RAFT agent from Example 3d The poly(acrylic acid)-block-poly(butyl acrylate) macro-RAFT agent solution from Example 3d (1.98 g of solution; containing 1.04 g, 0.31 mmol of macro-RAFT agent), butyl acrylate (5.67 g, 44.2 mmol), water (50 g) and sodium hydroxide (67 mg, 1.7 mmol) were mixed in a 100 mL beaker and vigorously stirred magnetically for 1 h. The resulting emulsion was subjected to ultrasonication for 2 minutes using Vibra-Cell Ultrasonic Processor (Sonics and Materials, Inc.) standard probe at 30% amplitude. The resulting miniemulsion was transferred to a 100 mL round bottom flask containing 4,4'-azobis(4-cyanopentanoic acid) (63 mg, 0.22 mmol). The flask was sealed with a with a rubber septum and stirred magnetically and sparged with nitrogen for 10 min, then heated at 70° in an oil bath. After 1 h, butyl acrylate (35.4 g, 276 mmol, deoxygenated by nitrogen sparging) was added to the reaction over 2 h using a syringe pump. At the end of the butyl acrylate addition, heating was continued for a further 1 h. The final latex had a solids content of 41% and an average particle size of 132 nm (HPPS).

EXAMPLE 4

Synthesis of 2-{[(dodecylsulfanyl)carbonothioyl]sulfanyl}propanoic Acid (15, $R^3$=$C_{12}H_{25}$)

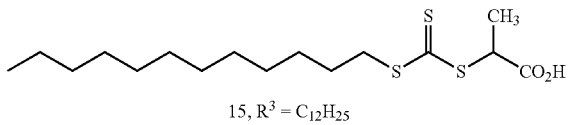

15, $R^3$ = $C_{12}H_{25}$

Dodecanethiol (2.50 g, 12.5 mmol), acetone (40 mL), and tetrapropylammonium bromide (0.27 g, 0.10 mmol) were added to a solution of sodium hydroxide (0.50 g, 12.5 mmol) in water (5 mL). The resulting solution was cooled in an ice bath and treated with carbon disulfide (0.75 mL, 0.95 g, 12.5 mmol). After 20 min, 2-bromopropanoic acid (1.91 g, 12.5 mmol) was added and the mixture was stirred at ambient temperature for 12 h. The solution was evaporated to ¼ volume and slowly acidified with 2 M hydrochloric acid (50 mL), then further diluted with water (150 mL). The resulting solid was collected and recrystallised from ether/light petroleum to give the title compound (15, $R^3$=$C_{12}H_{25}$) as yellow crystals (3.33 g, 76%).

EXAMPLE 4a

Preparation of a poly(acrylic acid) Macro-RAFT Agent With Degree of Polymerization n≈5 Using 2-{[(dodecylsulfanyl)carbonothioyl]sulfanyl}propanoic Acid (15, $R^3$=$C_{12}H_{25}$) From Example 4

2-{[(Dodecylsulfanyl)carbonothioyl]sulfanyl}propanoic acid (15, $R^3$=$C_{12}H_{25}$) (1.00 g, 2.86 mmol), 4,4'-azobis(4-cyanopentanoic acid) (82 mg, 0.29 mmol), and acrylic acid (1.03 g, 14.3 mmol) were dissolved in dioxane (4.0 g) in a round bottom flask and capped with a rubber septum. Nitrogen was bubbled through the solution for five minutes, after which it was immersed in an oil bath at 60° for 2 hours. $^1$H nmr spectroscopy and Electrospray Mass Spectrometry confirmed a degree of polymerization n≈5.

EXAMPLE 4b

Preparation of a poly(butyl acrylate) Latex Using the Macro-RAFT Agent from Example 4a The poly(acrylic acid) from Example 4a (1.07 g of solution, containing 0.36 g, 0.51 mmol of macro-RAFT agent), 4,4'-azobis(4-cyanopentanoic acid) (73 mg, 0.26 mmol), sodium hydroxide (104 mg, 2.6 mmol), and water (80.0 g) were added to a round bottom flask which was then sealed with a rubber septum. The solution was stirred magnetically and deoxygenated with a stream of bubbled nitrogen. The flask was immersed in an oil bath at 60° and the addition of butyl acrylate was started. The addition consisted of an initial shot of 0.10 g, followed by a continuous feed at 1.00 g/h for 2 h, followed by 5.97 g/h for a further 3 h to give a total addition of 20.0 g (0.156 mol). The reaction was allowed to proceed for another hour after the cessation of monomer feed to allow the polymerisation to reach high conversion. The resulting latex had 19.1% solids and the latex polymer had $\overline{M}_n$=57800 with $\overline{M}_w/\overline{M}_n$=1.79 (polystyrene standard).

EXAMPLE 4c

Preparation of a poly(butyl acrylate) Latex Directly from 2-{[(dodecylsulfanyl)carbonothioyl]sulfanyl}propanoic Acid (15, $R^3$=$C_{12}H_{25}$) from Example 4

2-{[(Dodecyclsulfanyl)carbonothioyl]sulfanyl}propanoic acid (15, $R^3$=$C_{12}H_{25}$) (182 mg, 0.520 mmol) and aqueous 25% tetramethylammonium hydroxide solution (223 mg, 0.614 mmol) were added to water (80.0 g) in a round bottom flask and the mixture was shaken to dissolve the RAFT reagent. 4,4'-Azobis(4-cyanopentanoic acid) 76 mg, 0.27 mmol) was then added and the flask was capped with a rubber septum and shaken. The solution was stirred magnetically and deoxygenated for 15 minutes with a stream of bubbled nitrogen. The flask was immersed in an oil bath at 60° and butyl acrylate addition was started. An initial shot (0.10 g) was followed by a continuous feed at 1.00 g/h for 2 h, then at 5.97 g/h for a further 3 h to give a total addition of 20.0 g (0.156 mol). The reaction was allowed to proceed for another hour after the cessation of monomer feed to allow the polymerisation to reach high conversion. Solids, molecular weight (polystyrene standard), and particle size (CHDF) data are given in the Table following.

| Reaction Time (min) | Solids Content | $\overline{M}_n$ (GPC) | $\overline{M}_w$ GPC) | Number Average Particle Diameter/nm (Polydispersity Index) |
|---|---|---|---|---|
| 30 | 0.51% | 344 | 379 | — |
| 60 | 0.58% | 864 | 906 | — |
| 90 | 0.82% | 1126 | 1193 | — |
| 120 | 1.39% | 1987 | 2200 | — |
| 150 | 2.06% | 3363 | 3643 | — |
| 180 | 2.81% | 4790 | 5301 | 51.7 (1.10) |
| 210 | 3.95% | 7181 | 8554 | 53.9 (1.11) |
| 240 | 7.69% | 16876 | 23416 | 60.6 (1.12) |
| 270 | 12.93% | 30679 | 59970 | 65.7 (1.21) |
| 300 | 18.22% | 44845 | 103824 | 77.2 (1.10) |
| 330 | 20.74% | 54378 | 121785 | |
| 360 | 21.87% | 57295 | 141828 | 81.6 (1.12) |

EXAMPLE 5

Synthesis of 2-{[(butylsulfanyl)carbonothioyl]sulfanyl}succinic Acid (16, $R^3$=$C_4H_9$)

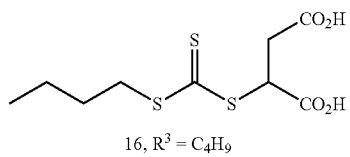

16, $R^3$ = $C_4H_9$

Triethylamine (13.9 mL, 10.1 g, 100 mmol) was added by syringe to a stirred solution of butanethiol (9.00 g, 100 mmol) and carbon disulfide (12.6 g, 10.0 mL, 166 mmol) in tetrahydrofuran (20 mL) in an Erlenmeyer flask. The reaction was stirred at ambient temperature for 1 h, then poured rapidly into a stirred solution of maleic acid (38.3 g, 330 mmol) in tetrahydrofuran (90 mL). The Erlenmeyer flask was rinsed with more tetrahydrofuran (ca 10 mL total) which was also added to the maleic acid solution. The reaction was stirred at ambient temperature for 0.5 h, then poured into water (200 mL) containing 3 M HCl (50 mL) and extracted with 3:1 (v/v) ether-dichloromethane (250 mL). The aqueous layer was decanted from some insoluble yellow material which was then extracted with more 3:1 (v/v) ether-dichloromethane (40 mL). The two organic extracts were combined and washed with water (6×250 mL), then extracted with 0.5 M sodium bicarbonate solution until the upper layer was no longer yellow (7×50 mL). The combined bicarbonate extracts were washed with dichloromethane (2×70 mL), then diluted with water to a total volume of 700 mL and acidified with 10 M HCl under vigorous (magnetic) stirring. After a few minutes the initial oily precipitate solidified. Stirring was continued overnight, and the product was collected by filtration, washed thoroughly with water, and air dried to give the title compound (16, R=$C_4H_9$) as bright yellow microcrystals, 24.0 g, 85%.

EXAMPLE 5a

Preparation of a poly(acrylic acid) Macro-RAFT Agent with Degree of Polymerization n≈15 Using 2-{[(butylsulfanyl)carbonothioyl]sulfanyl}succinic Acid (16, $R^3$=$C_4H_9$) from Example 5

A small glass vial was charged with 2-{[(butylsulfanyl)carbonothioyl]sulfanyl}succinic acid (16, $R^3$=$C_4H_9$) (0.564 g, 2.00 mmol), 4,4'-azobis(4-cyanopentanoic acid) (32 mg, 0.10 mmol), acrylic acid (2.16 g, 30.0 mmol), and water (5.40 g). A small magnetic stirring bar was included and the vial was stoppered with a rubber septum then stirred and sparged with nitrogen for 15 min. The reaction was then heated and stirred at 85° for 4 h to give, after cooling, a slightly viscous clear yellow solution containing 33% solids. The molecular weight ($\overline{M}_n$=1500) of the poly(acrylic acid) macro-RAFT agent was estimated from its $^1$H nmr spectrum.

EXAMPLE 5b

Preparation of a poly(butyl acrylate-co-styrene-co-acrylic Acid) Latex Using the Macro-RAFT Agent of Example 5a

| Stage | Material | Mass (g) | Weight % | mmol |
|---|---|---|---|---|
| A | Deionized water | 19.000 | 38.55 | |
| B | Solution of macro-RAFT agent from Example 5a | 0.244 | 0.50 | 0.16 |
| | Water component of macro-RAFT agent solution | 0.488 | 0.99 | |
| | 4,4'-azobis(4-cyanopentanoic acid) (V-501) | 0.025 | 0.05 | 0.08 |
| | Deionized water | 5.000 | 10.14 | |
| | 25% Ammonia (13.4 M) | 0.163 | 0.33 | 2.4 |
| C | Butyl acrylate | 3.060 | 6.21 | 23.9 |
| | Acrylic acid | 0.200 | 0.41 | 2.7 |
| | Styrene | 2.820 | 5.72 | 27.1 |
| D | Solution of macro-RAFT agent from Example 5a | 0.160 | 0.32 | 0.11 |
| | Water component of macro-RAFT agent solution | 0.320 | 0.65 | |
| | Deionized water | 3.000 | 6.09 | |
| | 25% Ammonia (13.4 M) | 0.109 | 0.22 | 1.6 |
| E | Butyl acrylate | 7.650 | 15.52 | 59.8 |
| | Styrene | 7.050 | 14.30 | 67.8 |
| | | 49.289 | 100.00 | |

A 100 mL round bottom flask containing a magnetic stirrer bar and Stage A was sealed with a rubber septum and deoxygenated with nitrogen for 30 min, then immersed in a heating bath at 85° for sufficient time to allow equilibration. Stage B, incorporating the macro-RAFT solution of Example 3a, was then added to the pre-equilibrated reaction flask. Stirring was started and Stage C was added via syringe in 1 mL portions over 5 min. After a further 0.5 h, the simultaneous additions of Stage D (in 0.5 mL portions at 20 min intervals via syringe) and Stage E (dropwise from a dropping funnel over 4 h) were started.

Heating and stirring were continued for an extra 2 h after the end of the addition of Stage E. The resulting latex was 39.0% solids and the latex polymer had $\overline{M}_n$=66400 with $\overline{M}_w/\overline{M}_n$=1.49 (polystyrene standard).

EXAMPLE 5c

Preparation of a poly(acrylic Acid) Macro-RAFT Agent with Degree of Polymerization n≈15 Using 2-{[(butylsulfanyl)carbonothioyl]sulfanyl}succinic Acid (16, $R^3$=$C_4H_9$) from Example 5

2-{[(Butylsulfanyl)carbonothioyl]sulfanyl}succinic acid (16, $R^3$=$C_4H_9$) (2.82 g, 10.0 mmol), 4,4'-azobis(4-cyanopentanoic acid) (0.28 g, 1.0 mmol), acrylic acid (10.8 g, 150 mmol), and water (41.8 g) were placed in a 100 mL round bottom flask containing a magnetic stirring bar. The flask was sealed with a rubber septum and stirred and sparged with nitrogen for 30 min, then heated and stirred at 85° for 5 h. The resulting yellow solution had 24.6% solids. The molecular weight ($\overline{M}_n$=1360, corresponding to a degree of polymerization n≈15) of the poly(acrylic acid) macro-RAFT agent, and unreacted monomer (<0.7%) were estimated by $^1$H nmr spectroscopy.

EXAMPLE 5d

Preparation of a poly(methyl methacrylate-co-styrene-co-butyl acrylate-co-acrylic acid) Latex Using the Macro-RAFT Reagent of Example 5c

| Stage | Material | Mass (g) | mmols | |
|---|---|---|---|---|
| A | Deionized water | 211.45 | | |
| B | poly(Acrylic acid) macro-RAFT agent from Example 5c | 10.85 | 1.96 | |
| | (meq. total acid in macro-RAFT agent) | | 33.31 | |
| | 4,4'-Azobis(4-cyanopentanoic acid) (V-501) | 0.254 | 0.81 | |
| | 25% Ammonia (13.4 M) | 1.70 | 24.99 | mL |
| C | Methyl methacrylate | 22.754 | 227.31 | |
| | Butyl acrylate | 20.562 | 160.39 | |
| | Styrene | 8.872 | 85.22 | |
| | Acrylic acid | 2.050 | 28.43 | |
| | 25% Ammonia (13.4 M) | 1.62 | 23.88 | mL |
| D | poly(Acrylic acid) macro-RAFT agent from Example 5c | 6.95 | 1.26 | |
| | (meq. total acid in macro-RAFT agent) | | 21.34 | |
| | Deionized water | 30.450 | | |
| | 25% Ammonia (13.4 M) | 1.09 | 16.00 | mL |
| E | Methyl methacrylate | 68.261 | 681.93 | |
| | Butyl acrylate | 61.686 | 481.17 | |
| | Styrene | 26.616 | 255.67 | |
| F | Deionized water | 10.500 | | |
| G | 25% Ammonia (13.4 M) | 2.450 | | |
| H | Tertiary butyl perbenzoate | 0.165 | drops | |
| I | Sodium erthyrobate | 0.240 | | |
| | DI water | 7.200 | | |
| J | Tertiary butyl perbenzoate | 0.165 | drops | |
| K | Tertiary butyl perbenzoate | 0.165 | drops | |
| L | Bevaloid 60 | 0.050 | drops | |
| M | Acticide | 1.000 | | |
| | Deionised water | 2.900 | | |
| | TOTAL | 500.00 | | |

Stage A was added to a 500 mL flask with a multi-neck top, fitted with a mechanical stirrer and reflux condenser. The flask was deoxygenated with nitrogen for 30 min, then immersed in a water bath at 80° for sufficient time to allow equilibration. An aliquot (ca 5 mL) was removed by syringe before commencement of heating to assist in the transfer of Stage B.

Stage B was made up in a small vial then added to the Stage A flask using the Stage A aliquot to rinse the vial.

Stage C was added via peristaltic pump over 15 minutes. The contents of the flask went cloudy within a few minutes.

After 15 minutes, the simultaneous additions of Stage D (over 1.5 h) and Stage E (over 3 h) were started. The monomer feed line was washed with Stage F and then Stage G was added. The reaction was heated and stirred for a further 30 minutes.

Stage H was added and Stage I was fed over 45 minutes. Stages J and K were added at 15 minute intervals.

The reaction was cooled to room temperature and Stages L and M were added.

The resulting latex had solids of 40.1%.

EXAMPLE 5e

Preparation of a poly(methyl methacrylate-co-butyl acrylate-co-trifluoroethyl methacrylate-co-acrylic acid) Latex Using the Macro-RAFT Reagent of Example 5c

| Stage | Material | Mass (g) | MW | mmol | |
|---|---|---|---|---|---|
| A | Deionised water] | 211.49 | | | |
| B | polyAA macro-RAFT agent from Example 5c | 10.85 | 1362 | 1.96 | |
|   | (meq. total acid in macro-RAFT agent) | | | 33.31 | |
|   | 4,4'-Azobis(4-cyanopentanoic acid) (V-501) | 0.254 | 312.5 | 0.81 | |
|   | 25% Ammonia (13.4 M) | 1.70 | 17 | 24.99 | mL |
| C | Butyl acrylate [calculated to be 7 × mols of 15-mer] | 1.76 | 128.2 | 13.72 | |
|   | TFEM [calculated to be 7 × mols of 15-mer] | 2.30 | 168 | 13.72 | |
| D | Methyl methacrylate | 31.004 | 100.1 | 309.74 | g |
|   | Butyl acrylate | 20.158 | 128.2 | 157.24 | mL |
|   | Styrene | 0.000 | 104.1 | 0.00 | min |
|   | Acrylic acid | 2.050 | 72.1 | 28.43 | |
|   | 25% Ammonia (13.4 M) | 1.62 | 17 | 23.88 | |
| E | polyAA macro-RAFT agent from Example 5c | 6.95 | 1362 | 1.26 | |
|   | (meq. total acid in macro-RAFT agent) | | | 21.34 | |
|   | Deionized water | 30.450 | | | |
|   | 25% Ammonia (13.4 M) | 1.09 | 17 | 16.00 | |
| F | Methyl methacrylate | 93.013 | 100.1 | 929.21 | mL |
|   | Butyl acrylate | 60.474 | 128.2 | 471.72 | min |
| G | Deionised water | 10.500 | | | |
| H | 25% Ammonia (13.4 M) | 2.450 | | | |
| I | Tertiary butyl perbenzoate | 0.165 | | 6.3 drops | |
| J | Sodium erythorbate | 0.240 | | | |
|   | Deionised water | 7.200 | | | |
| K | Tertiary butyl perbenzoate | 0.165 | | 6.3 drops | |
| L | Tertiary butyl perbenzoate | 0.165 | | 6.3 drops | |
| M | Bevaloid | 0.050 | | 1.9 drops | |
| N | Acticide | 1.000 | | | |
|   | Deionised water | 2.900 | | | |

Stage A was added to a 500 mL flask with a multi-neck top, fitted with a mechanical stirrer and reflux condenser. The flask was deoxygenated with nitrogen for 30 min, then immersed in a water bath at 85° for sufficient time to allow equilibration. An aliquot (ca 5 mL) was removed by syringe before commencement of heating to assist in the transfer of Stage B.

Stage B was made up in a small vial then added to the Stage A flask using the Stage A aliquot to rinse the vial.

Stage C was added dropwise over 1 minute and the reaction held for 20 minutes.

Stage D was added via peristaltic pump over 1 hour. The contents of the flask went cloudy within a few minutes.

The simultaneous additions of Stage E (over 1.5 h) and Stage F (over 3 h) were started.

The monomer feed line was washed with Stage G and then Stage H was added. The reaction was heated and stirred for a further 30 minutes.

Stage I was added and Stage H was fed over 45 minutes. Stages K and L were added at 15 minute intervals.

The reaction was cooled to room temperature and Stages M and N were added.

The finished latex had solids of 41.5%.

EXAMPLE 5f

Preparation of Paints Based on the RAFT Latex Prepared as Example 5e

| Stage | Material | Parts by weight |
|---|---|---|
| A | Deionised water | 3.65 |
|   | Propylene glycol | 1.60 |
|   | Bevaloid 60 | 0.15 |
|   | Aminomethyl propanol | 0.14 |
|   | Orotan 731A | 0.14 |
|   | Teric 460 | 0.70 |

-continued

| Stage | Material | Parts by weight |
|---|---|---|
| B | Tronox CR-826 | 18.20 |
|   | Omycarb 10 | 15.03 |
| C | Deionised water | 0.50 |
| D | Deionised water | 5.80 |

-continued

| Stage | Material | Parts by weight |
|---|---|---|
| E | Deionised water | 4.18 |
|   | Ropaque ultra | 8.33 |
|   | Latex from Example 5d | 34.14 |
|   | Bevaloid 60 | 0.02 |
|   | Proxel GXL | 0.08 |
|   | Amino methyl propanol | 0.09 |
| F | Propylene glycol | 2.00 |
|   | Natrosol Plus 330 | 0.30 |
| G | Texanol | 2.38 |
|   | Coasol | 0.80 |
|   | Bevaloid 60 | 0.31 |
| H | Acrysol RM-2020NPR | 0.28 |

Stage A ingredients were added in order with stirring order to a suitably sized vessel. Stage B ingredients were added and then dispersed at high speed for 20 min. The combined A and B stages were added to a separate vessel using the Stage C and D to wash out the dispersion vessel. Stage E ingredients were pre-mixed and added to the combined A-D with stirring, and the combination stirred for a further 20 minutes. Stage G was pre-mixed and added as a pencil stream, and the paint was finally adjusted with Stage H.

The experimental paint had weight solids 51.5%, volume solids 37.7% and pigment volume concentration of 50.5%.

The paint was applied side by side over a single sealed panel with a commercial premium quality interior waterborne white paint as a comparison. The paints were applied with a wire drawdown bar so as to achieve comparable film builds. The paints were dried for one hour at 50° and then a range of common household stains were applied to both films and left for one hour before removal with a conventional household spray cleaner. Stains were selected from a range of hydrophilic types, eg, coffee, red wine, waterborne marker and more hydrophobic character ie crayon, oil pastel, lipstick and a grease. The residues of stain left on the surface of the film were rated on the basis of the extent of removal:

| Stain | Commercial Control | Example 5e |
|---|---|---|
| Coffee | 3 | 3 |
| Red wine | 2 | 3 |
| Waterborne marker | 5 | 5 |
| Crayon | 1 | 3 |
| Oil pastel | 5 | 5 |
| Lipstick | 1 | 4 |
| Grease | 5 | 5 |

The paint of Example 5f, based on a the latex of Example 5e containing a fluorinated monomer added as part of the macro-RAFT stabilizer, shows stain resistance superior to the commercial control paint.

EXAMPLE 5g

Preparation of a poly(2-hydroxyethyl acrylate) Macro-RAFT Agent with Degree of Polymerization n≈15 using 2-{[(butylsulfanyl)carbonothioyl]sulfanyl}succinic Acid (16, $R^3=C_4H_9$) from Example 5

A 50 mL round bottom flask was charged with 4,4'-azobis (4-cyanopentanoic acid) (0.16 g, 0.50 mmol), 2-{[(butylsulfanyl)carbonothioyl]sulfanyl}succinic acid (16, $R^3=C_4H_9$) (1.41 g, 5.00 mmol), 2-hydroxyethyl acrylate (8.70 g, 75.0 mmol), and water (15.8 g). The flask was fitted with a rubber septum and the contents were stirred magnetically while being deoxygenated with nitrogen for 30 min. The flask was then immersed in a bath at 85° and stirred for 4 h, after which more water (15.0 g) was added. The resulting solution had 24.6% solids. $^1H$ nmr indicated a degree of polymerization n 15 and showed ca 1% unreacted 2-hydroxyethyl acrylate.

EXAMPLE 5b

Preparation of a poly(butyl acrylate-co-methyl methacrylate-co-acrylic acid) Latex Using the Macro-RAFT Agent of Example 5g

| Stage | Material | Mass (g) | Weight % | mMoles |
|---|---|---|---|---|
| A | polyHEA macro-RAFT agent from Example 5g | 0.404 | 0.93 | 0.20 |
|   | Water component of macro-RAFT agent solution | 1.213 | 2.79 |   |
|   | 4,4'-Azobis(4-cyanopentanoic acid) (V-501) | 0.032 | 0.07 | 0.10 |
| B | Deionized water | 25.000 | 57.41 |   |
| C | Butyl acrylate | 1.920 | 4.41 | 15.00 |
|   | Methyl methacrylate | 1.920 | 4.41 | 19.20 |
| D | Butyl acrylate | 6.400 | 14.70 | 50.00 |
|   | Acrylic acid | 0.259 | 0.60 | 3.60 |
|   | Methyl methacrylate | 6.400 | 14.70 | 64.00 |
|   | Formula total | 43.549 | 100.00 |   |

A 3-necked round bottom flask containing a magnetic stirrer bar was charged with Stages A and B, deoxygenated with nitrogen for 0.5 h, then immersed in a bath at 85° and stirred while adding Stage C (previously deoxygenated) via Hirschberg funnel over ca 1.5 h, followed by Stage D (previously deoxygenated) over ca 4 h. After cooling, removal of a small amount of coagulum (60 □m filter) gave a stable latex of 24.9% solids.

EXAMPLE 5i

Preparation of a Macro-RAFT Agent Based on a Copolymer of 2-hydroxyethyl Acrylate and methoxyPEG-7 Methacrylate with an Overall Degree of Polymerization n≈10 Using 2-{[(butylsulfanyl)carbonothioyl]sulfanyl}succinic Acid (16, $R^3=C_4H_9$) from Example 5

Sartomer CD-550 is the methacrylate ester of methoxypoly (ethylene glycol) which has an average degree of polymerization n≈7, as determined by $^1H$ nmr.

A 50 mL round bottom flask was charged with 4,4'-azobis (4-cyanopentanoic acid) (0.16 g, 0.50 mmol), 2-{[(butylsulfanyl)carbonothioyl]sulfanyl}succinic acid (16, $R^3=C_4H_9$) (1.41 g, 5.00 mmol), 2-hydroxyethyl acrylate (2.90 g, 25.0 mmol), Sartomer CD-550 (10.2 g, 25.0 mmol), and water (22.0 g). The flask was fitted with a rubber septum and the contents were stirred magnetically while being deoxygenated with nitrogen for 30 ml. The flask was then immersed in a bath at 60° and stirred for 4 h, after which more water (22.0 g) was added. The resulting solution had 24.4% solids. $^1$H nmr showed 3% unreacted 2-hydroxyethyl acrylate and no detectable CD-550.

EXAMPLE 5j

Preparation of a poly(butyl acrylate-co-methyl methacrylate-co-acrylic acid) Latex Using the Macro-RAFT Agent of Example 5i

| Stage | Material | Mass (g) | Weight % | mMoles |
|---|---|---|---|---|
| A | oly(HEA-co-CD-550) macro-RAFT agent from Example 5i | 0.566 | 1.28 | 0.20 |
|  | Water component of macro-RAFT agent solution | 1.698 | 3.83 |  |
|  | 4,4'-Azobis(4-cyanopentanoic acid) (V-501) | 0.127 | 0.29 | 0.40 |
| B | Deionized water | 25.000 | 56.45 |  |
| C | Butyl acrylate | 1.920 | 4.34 | 15.00 |
|  | Methyl methacrylate | 1.920 | 4.34 | 19.20 |
| D | Butyl acrylate | 6.400 | 14.45 | 50.00 |
|  | Acrylic acid | 0.259 | 0.59 | 3.60 |
|  | Methyl methacrylate | 6.400 | 14.45 | 64.00 |
|  | Formula total | 44.290 | 100.00 |  |

A 3-necked round bottom flask containing a magnetic stirrer bar was charged with Stages A and B, deoxygenated with nitrogen for 0.5 h, then immersed in a bath at 60° and stirred while adding Stage C (previously deoxygenated) via syringe pump over ca 1.5 h, followed by Stage D (previously deoxygenated) over ca 4 h. After cooling, removal of a small amount of coagulum (60 □m filter) gave a stable latex of 26.1% solids.

EXAMPLE 5k

Preparation of a Macro-RAFT Agent Based on a Copolymer of 2-hydroxyethyl Acrylate and methoxyPEG-11 Methacrylate with an Overall Degree of Polymerization n≈10 Using 2-{[(butylsulfanyl)carbonothioyl]sulfanyl}succinic Acid (16, $R^3$=$C_4H_9$) from Example 5

Sartomer CD-552 is the methacrylate ester of methoxypoly (ethylene glycol) which has an average degree of polymerization n≈11, as determined by $^1$H nmr.

A 50 mL round bottom flask was charged with 4,4'-azobis (4-cyanopentanoic acid) (0.16 g, 0.50 mmol), 2-{[(butylsulfanyl)carbonothioyl]sulfanyl}succinic acid (16, $R^3$=$C_4H_9$) (1.41 g, 5.00 mmol), 2-hydroxyethyl acrylate (2.90 g, 25.0 mmol), Sartomer CD-552 (14.6 g, 25.0 mmol), and water (29.0 g). The flask was fitted with a rubber septum and the contents were stirred magnetically while being deoxygenated with nitrogen for 30 min. The flask was then immersed in a bath at 85° and stirred for 4 h, after which more water (28.0 g) was added. The resulting solution had 24.9% solids. $^1$H nmr showed 2% unreacted 2-hydroxyethyl acrylate and no detectable CD-552.

EXAMPLE 5l

Preparation of a poly(butyl acrylate-co-methyl methacrylate-co-acrylic acid) Latex Using the Macro-RAFT Agent of Example 5k

| Stage | Material | Mass (g) | Weight % | mMoles |
|---|---|---|---|---|
| A | oly(HEA-co-CD-552) macro-RAFT agent from Example 5k | 0.742 | 1.65 | 0.20 |
|  | Water component of macro-RAFT solution | 2.226 | 4.95 |  |
|  | 4,4'-azobis(4-cyanopentanoic acid) (V-501) | 0.127 | 0.28 | 0.40 |
| B | Deionized water | 25.000 | 55.56 |  |
| C | Butyl acrylate | 1.920 | 4.27 | 15.00 |
|  | Methyl methacrylate | 1.920 | 4.27 | 19.20 |
| D | Butyl acrylate | 6.400 | 14.22 | 50.00 |
|  | Acrylic acid | 0.259 | 0.58 | 3.60 |
|  | Methyl methacrylate | 6.400 | 14.22 | 64.00 |
|  | Formula total | 44.994 | 100.00 |  |

A 3-necked round bottom flask containing a magnetic stirrer bar was charged with Stages A and B, deoxygenated with nitrogen for 0.5 h, then immersed in a bath at 70° and stirred while adding Stage C (previously deoxygenated) via syringe pump over ca 1.5 h, followed by Stage D (previously deoxygenated) over ca 4 h. After cooling, removal of a small amount of coagulum (60 □m filter) gave a stable latex of 23.4% solids.

EXAMPLE 6

Synthesis of 2-{[(dodecylsulfanyl)carbonothioyl]sulfanyl}succinic Acid (16, $R^3$=$C_{12}H_{25}$)

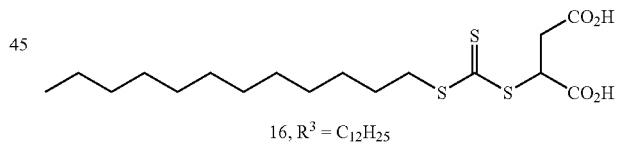

16, $R^3$ = $C_{12}H_{25}$

Triethylamine (13.0 mL, 9.4 g, 93 mmol) was added by syringe to a stirred solution of dodecanethiol (20.2 g, 100 mmol) and carbon disulfide (12.6 g, 10.0 mL, 166 mmol) in tetrahydrofuran (25 mL) in an Erlenmeyer flask. The reaction was stirred at ambient temperature for 1 h, then poured rapidly into a stirred solution of maleic acid (38.3 g, 330 mmol) in tetrahydrofuran (90 mL). The Erlenmeyer flask was rinsed with more tetrahydrofuran (ca 10 mL total) which was also added to the maleic acid solution. The reaction was stirred at ambient temperature for 0.5 h, then poured into water (200 mL) containing 3 M HCl (50 mL) and extracted with 3:1 (v/v) ether-dichloromethane (250 mL). The aqueous layer was decanted from some insoluble yellow material which was then extracted with more 3:1 (v/v) ether-dichloromethane (40 mL). The two organic extracts were combined, washed with water (4×250 mL), and evaporated. The crude product was dissolved in ethanol (150 mL) and added slowly to water (1200 mL) with vigorous (magnetic) stirring. Stirring was continued overnight, and the product was collected by filtration, washed thoroughly with water, air dried, and recrystallized from hexane containing a little ethanol to give the title compound (16, $R^3=C_{12}H_{25}$) as a yellow powder, 30.2 g, 77%.

EXAMPLE 6a

Preparation of a poly(butyl acrylate) Latex Using Unmodified 2-{[(dodecylsulfanyl)carbonothioyl]sulfanyl}succinic Acid (16, $R^3=C_{12}H_{25}$) from Example 6 as the Sole Stabilizer 2-{[(Dodecylsulfanyl)carbonothioyl]sulfanyl}succinic acid (0.206 g, 0.522 mmol), 4,4'-azobis(4-cyanopentanoic acid) (73 mg, 0.26 mmol), sodium hydroxide (42 mg, 1.06 mmol), and water (80.5 g) were added to a round bottom flask which was then sealed with a rubber septum. The solution was swirled to disperse the RAFT reagent and then stirred magnetically while the flask contents were deoxygenated with a stream of bubbled nitrogen. The flask was immersed in an oil bath at 60° and butyl acrylate addition was started. The addition consisted of an initial shot of 0.10 g, followed by a continuous feed at 1.00 g/h for 2 h, followed by 5.97 g/h for a further 3 h to give a total addition of 20.0 g (0.156 mol). The reaction was allowed to proceed for a further hour after the cessation of monomer feed to allow the polymerisation to reach higher conversion.

EXAMPLE 7

Synthesis of 2-{[(dodecylsulfanyl)carbonothioyl]sulfanyl}-2-methylpropanoic Acid (19, $R^3=C_{12}H_{25}$)

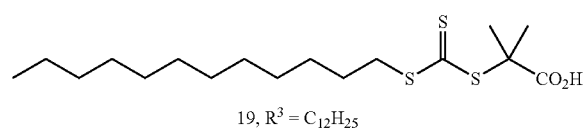

19, $R^3 = C_{12}H_{25}$

A stirred solution of dodecanethiol (12 mL, 50 mmol) and tetrapropylammonium bromide (0.54 g, 2.0 mmol) in acetone (30 mL) was treated with 50% sodium hydroxide solution (4.2 g, 53 mmol), followed by the slow addition of a solution of carbon disulfide (2.4 mL, 50 mmol) in acetone (10 mL). The mixture was stirred for 20 min by which time most of the solid had dissolved. Chloroform (6.0 mL, 25 mmol) was then added, followed by 50% sodium hydroxide solution (20 mL) and solid sodium hydroxide (2.5 g, 62.5 mmol). The flask was placed in a water bath to control the evolution of heat. After 2 h, the mixture was diluted with acetone (50 mL) and filtered. The collected solid was washed with acetone (2×25 mL). The combined filtrate and washings were evaporated to near dryness under reduced pressure then diluted with water (200 mL) and acidified to pH<1 with concentrated hydrochloric acid. The precipitate was collected, washed with water (2×30 mL) and dried. The resulting solid was dissolved in 50:50 ether/light petroleum (200 mL) and evaporated to near dryness. Light petroleum (50 mL) was added and resulting solution was kept at 4° overnight to crystallize the product. The desired trithiocarbonate (19, $R^3=C_{12}H_{25}$) was obtained as yellow crystals (5.31 g, 29%).

EXAMPLE 8

Synthesis of 2,2'-[(thioxomethylene)di(sulfanyl)]bis(2-methylpropanoic acid) (24)

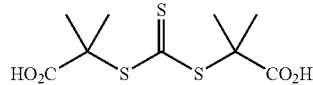

24

This compound was prepared according to the procedure of Lai, J. T.; Filla, D.; Shea, R. *Macromolecules* 2002, 35, 6754 and obtained as a fine yellow powder.

EXAMPLE 8a

Preparation of a poly(acrylic acid) Macro-RAFT Agent Having Two Hydrophilic Ends and with Degree of Polymerization n≈10 Using 2,2'-[(thioxomethylene)di(sulfanyl)]bis(2-methylpropanoic acid) (24) from Example 8

2,2'-[(Thioxomethylene)di(sulfanyl)]bis(2-methylpropanoic acid) (22) (0.150 g, 0.532 mmol), 4,4'-azobis(4-cyanopentanoic acid) (30 mg, 0.11 mmol), acrylic acid 0.388 g, 5.38 mmol), sodium hydroxide (42.5 mg, 1.06 mmol), water (2.00 g) and dioxane (1.00 g) were placed in a 10 mL round-bottom flask. The flask was sealed with a rubber septum and swirled to dissolve the contents. The resulting solution was deoxygenated by bubbling nitrogen through it for 5 min. The flask was then immersed in an oil bath at 60° and the polymerisation was allowed to proceed for 2 h.

EXAMPLE 8b

Preparation of a poly(butyl acrylate) Latex Using the Macro-RAFT Agent of Example 8a The poly(acrylic acid) solution from Example 8a (1.76 g of solution, containing 0.262 g, 0.262 mmol of macro-RAFT agent), 4,4'-azobis(4-cyanopentanoic acid (71 mg, 0.25 mmol), sodium hydroxide (83 mg (2.1 mmol) and g water (80.3 g) were placed in a round bottom flask which was then sealed with a rubber septum. The solution was swirled to disperse the RAFT agent and then stirred magnetically and deoxygenated with a stream of bubbled nitrogen. The flask was immersed in an oil bath at 60° and butyl acrylate addition was begun. An initial shot of 0.10 g, was followed by a continuous feed at 1.00 g/h for 2 h, followed by 5.97 g/h for a further 3 h, to give a total addition of 20.0 g (0.156 mol). Heating was continued for a further hour after the end of the of monomer addition.

EXAMPLE 9

Synthesis of 2-amino-1-methyl-2-oxoethyl butyl trithiocarbonate (25, $R^3=C_4H_9$)

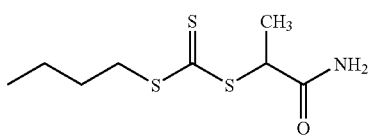

25, $R^3 = C_4H_9$

Acetone (230 mL), tetrapropylammonium bromide (1.86 g, 6.67 mmol), and butanethiol (9.3 mL, 7.8 g, 8.8 mmol)

were added to a solution of sodium hydroxide (3.5 g, 88 mmol) in water (12 mL), and the mixture was stirred in a stoppered flask for 20 min. Carbon disulfide (5.7 mL, 7.2 g, 95 mmol) was added and the solution was stirred for a further 20 min. 2-Bromopropionamide (13.3 g, 87.5 mmol) was added and the mixture was left for 14 h. The reaction was acidified with 2M hydrochloric acid (50 mL) and the volume was reduced to ca 100 mL by evaporation under reduced pressure. The residue was diluted with water (400 mL) and extracted with ethyl acetate (400 mL). The organic layer was washed with water (100 mL) and saturated sodium chloride (100 mL), dried with sodium sulfate and evaporated to dryness under reduced pressure. The residue was dissolved in ether (200 mL) and light petroleum (150 mL) and run through a 10 cm diameter Buchner funnel ¾ filled with silica gel. The filtrate was concentrated to ca ½ volume to give the title compound as a crop of yellow crystals (15.7 g, 76%). The silica gel was washed with ethyl acetate which was then combined with the mother liquors from the first crop of crystals. The resulting solution was evaporated to dryness under reduced pressure and partially purified by chromatography using ether/light petroleum. Recrystallisation from ether/light petroleum gave a second crop of the trithiocarbonate (3.76 g, 18%). An analytically pure sample was obtained by recrystallisation of the combined crops from ether/light petroleum (17.5 g, 84%).

EXAMPLE 9a

Preparation of a Polyacrylamide Macro-RAFT Agent with Degree of Polymerization n≈15 Using 2-amino-1-methyl-2-oxoethyl butyl trithiocarbonate (25, $R^3=C_4H_9$) from Example 9

2-Amino-1-methyl-2-oxoethyl butyl trithiocarbonate (25, $R^3=C_4H_9$) (0.556 g, 2.34 mol), 2,2'-azobis{2-methyl-N-[1,1-bis(hydroxymethyl)-2-hydroxyethyl]propionamide}, (97 mg, 0.024 mmol), acrylamide (2.50 g, 35.2 mmol), dioxane (15.2 g), and water (5.01 g) were added to a 10 mL round-bottom flask. This was capped with a rubber septum and swirled to dissolve the RAFT agent, and the resulting solution was deoxygenated by bubbling nitrogen through it for 5 min. The flask was then immersed in an oil bath at 60° for 2 h then at 85° for a further 2 h to effect polymerization

EXAMPLE 9b

Preparation of a Non-Ionically Stabilized poly(butyl acrylate) Using the Polyacrylamide Macro-RAFT Agent from Example 9a The polyacrylamide macro-RAFT agent solution from Example 9a (4.40 g of solution, containing 0.524 mmol of macro-RAFT agent), 2,2'-azobis{2-methyl-N-[1,1-bis(hydroxymethyl)-2-hydroxyethyl]propionamide} (0.105 g, 0.257 mmol), sodium chloride (0.153 g, 2.62 mmol,) and water (80.0 g) were added to a round bottom flask which was then sealed with a rubber septum. The solution was swirled to disperse the RAFT agent and then stirred magnetically while the flask contents were deoxygenated with a stream of bubbled nitrogen. The flask was immersed in an oil bath at 75° and butyl acrylate addition was started with an initial shot of 0.10 g, followed by a continuous feed at 1.00 g/h for 2 h, followed by 5.97 g/h for a further 3 h to give a total addition of 20.0 g (0.156 mol). Heating was continued for 1 h after the end of the monomer feed to allow the polymerisation to reach high conversion.

EXAMPLE 9c

Preparation of a poly(acrylamide)-block-polystyrene Macro-RAFT Agent with Respective Degrees of Polymerization n≈25 and n≈13 using 2-amino-1-methyl-2-oxoethyl butyl trithiocarbonate (25, $R^3=C_4H_9$) from Example 9

A solution of 2-amino-1-methyl-2-oxoethyl butyl trithiocarbonate (0.233 g, 0.983 mmol), 2,2'-azobis {2-methyl-N-[1,1-bis(hydroxymethyl)-2-hydroxyethyl]propionamide} (0.042 g, 0.102 mmol) and acrylamide (1.78 g, 25.1 mmol) in dioxane (10 g) and water (3.1 g) in a 50 mL round bottomed flask was stirred magnetically and sparged with nitrogen for 5 min. The flask was then heated at 80° for 1.5 h. At the end of this period, styrene (2.02 g, 19.4 mmol) was added to the flask and heating was continued at 80° for a further 20 h. The resulting copolymer solution had 19.7% solids.

EXAMPLE 9d

Preparation of a poly(styrene-co-divinylbenzene) Suspension Polymer Using the Macro-RAFT Agent from Example 9c 2,2'-Azobis(isobutyronitrile) (0.48 g, 2.9 mmol), was dissolved in styrene (41.3 g, 0.40 mol) and divinylbenzene (0.58 g, 4.5 mmol), in a 250 mL bottle using an ultrasonic bath. When a clear solution was obtained, the diblock copolymer solution from Example 9c (1.7 g of solution; containing 0.33 g, 0.098 mmol of macro-RAFT agent), and water (157 g) were added and the mixture was intermittently shaken vigorously over a period of 10 minutes. The crude dispersion thus obtained was recycled through an Avestin Emulsiflex C50 homogeniser operating at 15,000 psi for a period of 5 minutes. The resulting emulsion was transferred to a 250 mL round bottomed flask, sparged with nitrogen for 5 min, stirred with an overhead stirrer at 138 rpm, and heated to 70° in a water bath. The reaction was continued at that stirring rate and temperature and under a nitrogen blanket for 21 h. A dispersion of particles with particle sizes substantially in the range of 1 to 10 □m (as estimated by light microscopy) was obtained.

EXAMPLE 9e

Preparation of a poly(N,N-dimethylaminoethyl methacrylate) Macro-RAFT Agent Having Degree of Polymerization n 5 Using 2-amino-1-methyl-2-oxoethyl butyl trithiocarbonate (25, $R^3=C_4H_9$) from Example 9

2-Amino-1-methyl-2-oxoethyl butyl trithiocarbonate (25, $R^3=C_4H_9$) (0.288 g, 121 mmol), 2,2'-azobis(2-methylpropionamidine)dihydrochloride (34 mg, 0.13 mmol), N,N-dimethylaminoethyl methacrylate (DMAEMA) (0.956 g, 6.09 mmol), dioxane (2.25 g), and water (2.24 g) were placed in a 10 mL round-bottom flask. The flask was capped with a rubber septum and swirled to dissolve the RAFT Agent, and the solution was deoxygenated by bubbling nitrogen through it for 5 min. The flask was then immersed in an oil bath at 60° for 2.5 h for the polymerisation to proceed.

EXAMPLE 9f

Preparation of a Cationically Stabilized poly(butyl acrylate) Latex Using the polyDMAEMA macro-RAFT agent from Example 9e The polyDMAEMA macro-RAFT agent solution from Example 9e (2.47 g of solution, containing 0.52 mmol of macro-RAFT agent), 2,2'-azobis(2-methylpropionamidine) dihydrochloride (71 mg, 0.26 mmol), 32% hydrochloric acid (0.210 g, 1.84 mmol), and water (80.1 g) were placed in a round bottom flask which was then sealed with a rubber septum and swirled to disperse the RAFT agent. The resulting solution was then stirred magnetically while being deoxygenated with a stream of bubbled nitrogen. The flask was immersed in an oil bath at 60° and butyl acrylate addition was started. An initial shot of 0.10 g was followed by a continuous feed at 1.00 g/h for 2 h, then by a feed at 5.97 g/h for a further 3 h to give a total addition of 20.0 g (0.156 mol). Heating was continued for another hour after the end of the monomer feed to allow the polymerisation to reach high conversion.

EXAMPLE 10

Synthesis of benzyl 2-[(2-hydroxyethyl)amino]-1-methyl-2-oxoethyl trithiocarbonate

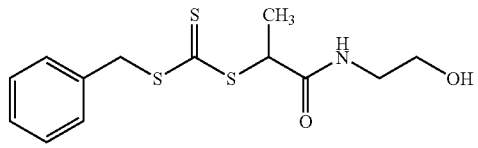

A solution of sodium hydroxide (1 g; 25 mmol) in water (5 mL) was added to acetone (70 mL), followed by tetrapropylammonium bromide (0.53 g; 20 mmol) and then benzyl mercaptan (3.11 g; 25 mmol; 2.94 mL) with stirring. After 20 min carbon disulfide (2.12 g; 27.5 mmol; 1.76 mL) was added dropwise, causing a bright yellow colouration. After stirring the resulting solution for an additional 15 min, 2-bromopropanoic acid (3.83 g; 25 mmol; 2.26 mL) was added dropwise and then the whole was stirred for 17 h. Acetone and excess carbon disulfide were removed under high vacuum until a cloudy yellow mixture was obtained. This was diluted with water (100 mL) and acidified with 2 M HCl. The resulting yellow oil was extracted into ether, the combined extracts were dried (Na$_2$SO$_4$) and the solvent was removed under high vacuum. The remaining viscous liquid was distilled (80°/0.13 Pa, Kugelrohr) to remove unreacted 2-bromopropanoic acid, leaving a 2-{[benzylsulfanyl)carbonothioyl]sulfanyl}propanoic acid as a viscous oil that solidified on standing (3.71 g; 54%). This compound (13.6 mmol), was dissolved in tetrahydrofuran (40 mL) and treated with 1,1'-carbonyldiimidazole (2.64 g; 16.3 mmol) portionwise as a solid, and then the whole was stirred at room temperature for 30 min until CO$_2$ liberation ceased. The resulting solution was then cooled to −50° and treated with ethanolamine (1.00 g; 16.3 mmol; 0.98 mL) dropwise. The reaction mixture was stirred overnight while warming to room temperature. The tetrahydrofuran was removed under high vacuum and the heterogeneous residue was dissolved in ethyl acetate (80 mL) and washed with water (2×40 mL). The organic layer was dried (Na$_2$SO$_4$) and evaporated under high vacuum to give an orange liquid which was submitted to flash chromatography on silica (ethyl acetate). The product was obtained as a yellow oil (0.91 g; 21%). Trituration with hexane/ether gave the title compound as a fine light yellow powder (0.69 g).

EXAMPLE 11

Synthesis of 3-{[(tert-butylsulfanyl)carbonothioyl]sulfanyl}propanoic Acid

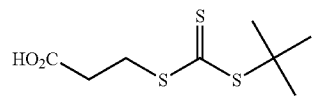

A solution of sodium hydroxide (1.0 g; 25 mmol) in water (5 mL) was added to acetone (70 mL) followed by tetrapropylammonium bromide (0.53 g; 20 mmol) and then tert-butyl mercaptan (2.26 g; 25 mmol; 2.82 mL) with stirring forming a white precipitate. After 20 min. carbon disulfide (2.12 g; 27.5 mmol; 1.67 mL) was added dropwise causing the precipitate to slowly disappear and an orange solution to form. After stirring the resulting solution for an additional 40 min, 2-bromopropanoic acid (3.83 g; 25 mmol; 2.26 mL) was added dropwise and then the whole was stirred for 18 h. Acetone and excess carbon disulfide were removed under high vacuum to give an orange oil. This was diluted with water (100 mL) giving an aqueous solution of pH 4. This was extracted with ether, the combined extracts were dried (Na$_2$SO$_4$) and the solvent was removed under high vacuum. The remaining viscous orange oil was frozen in liquid nitrogen and kept in the freezer for 20 h during which time a solid mass developed. The solid was triturated with hexane with stirring for 2 h and then filtered, washing with more hexane. The title compound was obtained as a yellow solid (2.06 g; 35%).

EXAMPLE 11a

Preparation of a poly(butyl acrylate) Latex Directly from 3-{[(tert-butylsulfanyl)carbonothioyl]sulfanyl}Propanoic Acid from Example 11

3-{[(tert-Butylsulfanyl)carbonothioyl]sulfanyl}propanoic acid (0.123 g, 0.517 mmol), a 25% aqueous solution of trimethylammonium hydroxide (0.187 g, 0.512 mmol), and water (80.5 g) were placed in a 100 mL round-bottom flask and sonicated in a sonic bath for 5 min to dissolve the RAFT reagent. 4,4'-Azobis(4-cyanopentanoic acid) (83 mg, 0.30 mmol) was next added to the flask which was then sealed with a rubber septum and swirled to disperse the initiator. The resulting solution was then stirred magnetically while being deoxygenated with a stream of bubbled nitrogen for 5 min. The flask was immersed in an oil bath at 60° and butyl acrylate addition was started. An initial shot of 0.10 g was followed by a continuous feed at 1.00 g/h for 2 h, then by a feed at 5.97 g/h for a further 3 h to give a total addition of 20.0 g (0.156 mol). Heating was continued for another hour after the end of the monomer feed to allow the polymerisation to reach high conversion.

The reference to any prior art in this specification is not, and should not be taken as, an acknowledgment or any form of suggestion that that prior art forms part of the common general knowledge in Australia.

Throughout this specification and the claims which follow, unless the context requires otherwise, the word "comprise", and variations such as "comprises" and "comprising", will be understood to imply the inclusion of a stated integer or step or group of integers or steps but not the exclusion of any other integer or step or group of integers or steps.

Those skilled in the art will appreciate that the invention described herein is susceptible to variations and modifications other than those specifically described. It is to be understood that the invention includes all such variations and modifications which fall within the spirit and scope. The invention also includes all of the steps, features, compositions and compounds referred to or indicated in this specification, individually or collectively, and any and all combinations of any two or more of said steps or features.

The invention claimed is:

1. A method for preparing an aqueous dispersion of polymer particles comprising the following steps:
   (i) preparing a dispersion having a continuous aqueous phase, a dispersed organic phase comprising one or more ethylenically unsaturated monomers, and an amphiphilic RAFT agent as a stabilizer for said organic phase, and
   (ii) polymerising said one or more ethylenically unsaturated monomers under the control of said amphiphilic RAFT agent to form said aqueous dispersion of polymer particles.

2. The method according to claim 1, wherein the dispersion of step (i) is prepared by forming a solution of amphiphilic RAFT agent in water and polymerising added ethylenically unsaturated monomer under the control of the amphiphilic RAFT agent.

3. The method according to claim 1, wherein the dispersion of step (i) is prepared by forming a composition comprising water insoluble amphiphilic RAFT agent and ethylenically unsaturated monomer, and combining this composition with water.

4. The method according to claim 3, wherein the RAFT agent is dissolved in monomer, optionally together with organic solvent.

5. The method according to claim 1, wherein the dispersion of step (i) is prepared by forming a composition comprising water insoluble amphiphilic RAFT agent and water, and combining this composition with ethylenically unsaturated monomer.

6. The method of any one of claims 1 to 5 wherein the amphiphilic RAFT agent is of general formula (4):

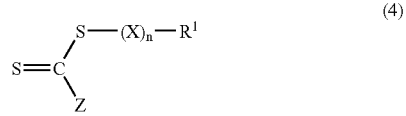

(4)

where each X is independently a polymerised residue of an ethylenically unsaturated monomer, n is an integer ranging from 0 to 100, $R^1$ is an organic group optionally substituted with one or more hydrophilic groups and Z is any group that can promote sufficient reactivity of the thiocarbonyl group towards radical addition while not slowing the rate of fragmentation to the extent that there is unacceptable retardation of polymerisation.

7. The method according to claim 6 wherein $R^1$ is selected from $C_1$-$C_6$ alkyl, $C_1$-$C_6$ alkoxy aryl or heteroaryl, each of which is substituted with one or more hydrophilic groups selected from —$CO_2H$, —$CO_2R'$, —$SO_3H$, —$OSO_3H$, —SOR', —$SO_2R'$, —$OP(OH)_2$, —$P(OH)_2$, —$PO(OH)_2$, —OH, —OR', —$(OCH_2$—$CHR)_w$—OH, —$CONH_2$, CONHR', CONR'R", —NR'R", —N+R'R"R'", where R is selected from $C_1$-$C_6$ alkyl, w is 1 to 10, R', R" and R'" are independently selected from alkyl and aryl which are optionally substituted with one or more hydrophilic substituents selected from —$CO_2H$, —$SO_3H$, —$OSO_3H$, —OH, —$(COCH_2CHR)_w$—OH, —$CONH_2$, —SOR and $SO_2R$, and salts thereof, and wherein Z is selected from optionally substituted aryl, optionally substituted heterocyclyl, optionally substituted arylalkyl, optionally substituted alkylthio, optionally substituted arylalkylthio, dialkoxy- or diaryloxy-phosphinyl [—$P(=O)OR^2_2$], dialkyl- or diaryl-phosphinyl [$P(=O)R^2_2$], optionally substituted acylamino, optionally substituted acylimino, optionally substituted amino, $R^1$—$(X)_n$—S— and a polymer chain formed by any mechanism; wherein $R^1$; X and n are as defined herein or in claim 6, and $R^2$ is selected from the group consisting of optionally substituted $C_1$-$C_{18}$ alkyl, optionally substituted $C_2$-$C_{18}$ alkenyl, optionally substituted aryl, optionally substituted heterocyclyl, optionally substituted aralkyl, and optionally substituted alkaryl.

8. The method of any one of claims 1 to 5 wherein the amphiphilic RAFT agent is of general formula (4):

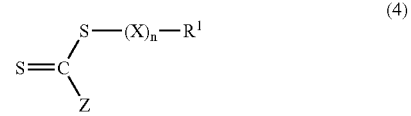

(4)

where each X is independently a polymerised residue of an ethylenically unsaturated monomer, n is an integer ranging from 0 to 100, Z is any group that can promote sufficient reactivity of the thiocarbonyl group towards radical addition while not slowing the rate of fragmentation to the extent that there is unacceptable retardation of polymerization, and wherein $R^1$ is an organic group substituted with one or more hydrophobic groups.

9. A method of preparing a paint, filler, adhesive, primer or sealant comprising preparing a dispersion according to any one of claims 1 to 5, and combining the dispersion with one or more formulation components.

10. A method of preparing a paint, filler, adhesive, primer or sealant comprising preparing a dispersion according to claim 6 and combining the dispersion with one or more formulation components.

11. A method of preparing a paint, filler, adhesive, primer or sealant comprising preparing a dispersion according to claim 7 and combining the dispersion with one or more formulation components.

12. A method of preparing a paint, filler, adhesive, primer or sealant comprising preparing a dispersion according to claim 8 and combining the dispersion with one or more formulation components.

* * * * *